US012623002B2

(12) United States Patent
Freytes et al.

(10) Patent No.: US 12,623,002 B2
(45) Date of Patent: May 12, 2026

(54) FAST AUTOMATED APPROACH FOR THE DERIVATION OF ACELLULAR EXTRACELLULAR MATRIX SCAFFOLDS FROM TISSUES

(71) Applicant: North Carolina State University, Raleigh, NC (US)

(72) Inventors: Donald O. Freytes, Cary, NC (US); Camilo A. Mora-Navarro, Raleigh, NC (US); Andreea Badileanu, Garner, NC (US)

(73) Assignee: North Carolina State University, Raleigh, NC (US)

( * ) Notice: Subject to any disclaimer, the term of this patent is extended or adjusted under 35 U.S.C. 154(b) by 686 days.

(21) Appl. No.: 17/925,187

(22) PCT Filed: May 14, 2021

(86) PCT No.: PCT/US2021/032593
§ 371 (c)(1),
(2) Date: Nov. 14, 2022

(87) PCT Pub. No.: WO2021/231956
PCT Pub. Date: Nov. 18, 2021

(65) Prior Publication Data
US 2023/0181796 A1 Jun. 15, 2023

Related U.S. Application Data

(60) Provisional application No. 63/024,870, filed on May 14, 2020.

(51) Int. Cl.
| | |
|---|---|
| *A61L 27/36* | (2006.01) |
| *C12M 1/00* | (2006.01) |
| *C12M 1/06* | (2006.01) |
| *C12M 1/26* | (2006.01) |
| *C12M 1/34* | (2006.01) |
| *C12M 1/36* | (2006.01) |

(52) U.S. Cl.
CPC ....... *A61L 27/3683* (2013.01); *A61L 27/3633* (2013.01); *C12M 27/02* (2013.01); *C12M 33/14* (2013.01); *C12M 41/12* (2013.01); *C12M 41/32* (2013.01); *C12M 41/44* (2013.01); *C12M 41/48* (2013.01); *C12M 45/06* (2013.01); *C12M 45/09* (2013.01); *A61L 2400/06* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 8,691,276 B2 | 4/2014 | Badylak et al. | |
| 9,084,722 B2 | 7/2015 | Gilbert et al. | |
| 2013/0177972 A1* | 7/2013 | Green | G06K 19/067 |
| | | | 235/487 |
| 2017/0260498 A1 | 9/2017 | Mundt et al. | |
| 2019/0339257 A1 | 11/2019 | Radisic | |

FOREIGN PATENT DOCUMENTS

| | | |
|---|---|---|
| WO | WO 2019/060518 A1 | 3/2019 |
| WO | WO 2019/168913 A1 | 9/2019 |
| WO | WO 2019/236622 A1 | 12/2019 |

OTHER PUBLICATIONS

Andenaes, K., et al., "The extracellular matrix proteoglycan fibromodulin is upregulated in clinical and experimental heart failure and affects cardiac remodeling," Plos One, vol. 13, No. 7, 2018.

Badileanu, et al., "Fast Automated Approach for the Derivation of Acellular Extracellular Matrix Scaffolds from Porcine Soft Tissues," ACS Biomater Sci Eng. 13; 6(7): p. 1-30, 2020.

Badylak, S.., Extracellular matrix as a biological scaffold material: Structure and function. Acta Biomater, vol. 5 No. 1, pp. 1-13, 2009.

Brown, B. N., et al., "Extracellular matrix as an inductive scaffold for functional tissue reconstruction," Transl Res 2014, 163 (4), 268-285.

Brunner-La Rocca, H. P., et al., "Therapeutic benefits of increasing natriuretic peptide levels," Cardiovasc Res, vol. 51, No. 3, pp. 510-520 2001.

Choudhury, D., et al., "Organ-Derived Decellularized Extracellular Matrix: A Game Changer for Bioink Manufacturing?," Trends Biotechnol , vol. 36, No. 8, pp. 787-805, 2018.

Christensen, G.; et al., "Sweet, yet underappreciated: Proteoglycans and extracellular matrix remodeling in heart disease," Matrix Biol 75-76, pp. 286-299, 2019.

Cramer, M. C.; Badylak, S. F., Extracellular Matrix-Based Biomaterials and Their Influence Upon Cell Behavior. Ann Biomed Eng 2019. DOI: 10.1007/s10439-019-02408-9.

Crapo, P. M., et al., "An overview of tissue and whole organ decellularization processes," Biomaterials, vol. 32 No. 12, pp. 3233-3243, 2011.

Dzobo, K., et al., "Recent Trends in Decellularized Extracellular Matrix Bioinks for 3D Printing: An Updated Review," Int J Mol Sci, vol. 20, No. 18, 2019.

Efraim, Y., et al., 3D Structure and Processing Methods Direct the Biological Attributes of ECM-Based Cardiac Scaffolds. Sci Rep-Uk 2019, 9.

Fernandez-Perez, J.; et al., Author Correction: The impact of decellularization methods on extracellular matrix derived hydrogels., Sci Rep 2019, 9 (1), 19818.

(Continued)

*Primary Examiner* — Nannette Holloman

(74) *Attorney, Agent, or Firm* — Jenkins, Taylor & Hunt, P.A.

(57) ABSTRACT

Provided herein are systems, devices and methods to automate and optimize the decellularization process of representative tissues, such as soft tissues, for extracellular matrix (ECM)-based scaffold and biomaterial production. The automated decellularization processes and devices significantly reduce the exposure time to reagents, minimize lot-to-lot variability, and largely preserve the native composition of the ECM from the decellularized tissue or species.

33 Claims, 16 Drawing Sheets

(56)                    References Cited

OTHER PUBLICATIONS

Freytes, D. O., et al., "Natural Cardiac Extracellular Matrix Hydrogels for Cultivation of Human Stem Cell-Derived Cardiomyocytes," Radisic, M.; Black Iii, L. D., Eds. Springer New York: New York, NY, 2014; vol. 1181, pp. 69-81.

Gilpin, A., "Decellularization Strategies for Regenerative Medicine: From Processing Techniques to Applications," Biomed Research International 2017.

Hernandez, M. J., et al., "Manufacturing considerations for producing and assessing decellularized extracellular matrix hydrogels," Methods 2019.

Huleihel, L., et al., "Matrix-Bound Nanovesicles Recapitulate Extracellular Matrix Effects on Macrophage Phenotype," Tissue Eng Pt A 2017, 23 (21-22), 1283-1294.

Huleihel, L., et al., "Matrix-bound nanovesicles within ECM bioscaffolds," Sci Adv 2016, 2 (6).

Hussey, G. S., et al., "Matrix bound nanovesicle-associated IL-33 activates a pro-remodeling macrophage phenotype via a non-canonical, ST2-independent pathway," Journal of Immunology and Regenerative Medicine 2019, 3, 26-35,.

International Search Report and Written Opinion corresponding to International Application No. PCT/US2021/032593 dated Oct. 7, 2021, p. 7.

International Preliminary Report on Patentability corresponding to International Application No. PCT/US2021/032593 dated Nov. 15, 2022.

Jimenez-Gastelum, G. R., "Antimicrobial Properties of Extracellular Matrix Scaffolds for Tissue Engineering," Biomed Res Int 2019, 2019, 9641456.

Kusuma, G. D., et al., "Transferable Matrixes Produced from Decellularized Extracellular Matrix Promote Proliferation and Osteogenic Differentiation of Mesenchymal Stem Cells and Facilitate Scale-Up," Acs Biomater Sci Eng 2018, 4 (5), 1760-1769.

Mora-Navarro, C., et al., Porcine Vocal Fold Lamina Propria-Derived Biomaterials Modulate TGF-$\beta$1-Mediated Fibroblast Activation in Vitro. Acs Biomater Sci Eng 2020.

Palmer, B. F. et I., An Emerging Role of Natriuretic Peptides: Igniting the Fat Furnace to Fuel and Warm the Heart. Mayo Clinic Proceedings 2015, 90 (12), 1666-1678.

Pellegata, A. F., et al., A novel device for the automatic decellularization of biological tissues. Int J Artif Organs 2012, 35 (3), 191-198.

Sackett, S. D., et al., Extracellular matrix scaffold and hydrogel derived from decellularized and delipidized human pancreas. Sci Rep 2018, 8 (1), 10452.

Saldin, L. T., et al., Extracellular matrix hydrogels from decellularized tissues: Structure and function. Acta Biomater 2017, 49, 1-15.

Sarker, B., et al., Evaluation of Fibroblasts Adhesion and Proliferation on Alginate-Gelatin Crosslinked Hydrogel. Plos One 2014, 9 (9).

Shah, M., et al., A Thin Layer of Decellularized Porcine Myocardium for Cell Delivery. Sci Rep-Uk 2018, 8.

Simsa, R., et al., Systematic in vitro comparison of decellularization protocols for blood vessels. Plos One 2018, 13 (12).

Singelyn, J. M., et al., Naturally derived myocardial matrix as an injectable scaffold for cardiac tissue engineering. Biomaterials 2009, 30 (29), 5409-5416.

Song, W., et al., Atrial natriuretic peptide in cardiovascular biology and disease (NPPA). Gene 2015, 569 (1), 1-6.

Spang, M. T., et al., Extracellular matrix hydrogel therapies: In vivo applications and development. Acta Biomater 2018, 68, 1-14.

Traverse, J. H., et al., First-in-Man Study of a Cardiac Extracellular Matrix Hydrogel in Early and Late Myocardial Infarction Patients. JACC: Basic to Translational Science 2019, 357.

Tse, J. R.;, et al., Microstructure Characterization of a Decellularized Vocal Fold Scaffold for Laryngeal Tissue Engineering. Laryngoscope 2014, 124 (8), E326-E331.

Wade, R. J., et al., Engineering ECM signals into biomaterials. Mater Today 2012, 15 (10), 454-459.

Wu et al., (2017) "Lung Protection by inhalation of exogenous solubilized extracellular matrix," Plos ONE; 15 Pages.

Wisniewski, J. R., et al., Universal sample preparation method for proteome analysis. Nature Methods 2009, 6 (5), 359-U60.

Wrona, E. A., et al., Derivation and characterization of porcine vocal fold extracellular matrix scaffold. Laryngoscope 2016, 126 (4), 928-35.

Zheng, Z., et al., Fibromodulin reduces scar formation in adult cutaneous wounds by eliciting a fetal-like phenotype. Signal Transduct Tar 2017, 2.

Zheng, Z.; K et al., Fibromodulin Enhances Angiogenesis during Cutaneous Wound Healing. Prs-Glob Open 2014, 2 (12).

Zhu, M., et al., "In vivo engineered extracellular matrix scaffolds with instructive niches for oriented tissue regeneration," Nat Commun 2019, 10 (1), 4620.

* cited by examiner mVFLP-ECM

1.) 4% SODIUM DEOXYCHOLATE
2.) DNAse (273 KUNITZ/mL)
3.) 0.1% PERACETIC ACID

|  |  |  |
| :---: | :---: | :---: |
| 1 | 2 | 3 |
| 30 MIN | 30 MIN | 30 MIN |

▨ 5 MIN DI WATER + 5 MIN 2X DPBS

▧ 15 MIN 1X DPBS + 15 MIN 1X DPBS

IN SITU ECM SOLUBILIZATION
(PRE-HYDROGEL)

GOMORI'S TRICHROME

<300 μm

NEBULIZED ECM

NEBULIZED PARTICLE SIZE
MESH 0.25X OF ECM

CELL ATTACHMENT TEST
NEBULIZED 1X ECM        NEBULIZED PBS CONTROL

NON TISSUE CULTURE TREATED SURFACES

FAST AUTOMATED APPROACH FOR THE DERIVATION OF ACELLULAR EXTRACELLULAR MATRIX SCAFFOLDS FROM TISSUES

CROSS REFERENCE TO RELATED APPLICATIONS

This application is a U.S. National Phase Application of PCT International Patent Application No. PCT/US2021/032593, filed May 14, 2021, incorporated herein by reference in its entirety, and which claims benefit of U.S. Provisional Patent Application Ser. No. 63/024,870, filed May 14, 2020, the disclosure of which is incorporated herein by reference in its entirety.

STATEMENT OF GOVERNMENT SUPPORT

This invention was made with government support under grant numbers DC017139 and DC017743 awarded by the National Institutes of Health. The government has certain rights in the invention.

TECHNICAL FIELD

Provided herein are fast automated approaches for the derivation of acellular extracellular matrix scaffolds from tissues. Devices, systems and methods for deriving acellular extracellular matrix scaffolds from tissues are provided.

BACKGROUND

Limited availability of donor tissues and/or organs for allotransplantation combined with an increase in donor site morbidity risk associated with autografting, have led to a high demand for off-the-shelf tissue replacements.[1] Extracellular matrix (ECM) scaffolds are complex, three-dimensional, heterogeneous networks of structural and functional proteins (e.g., collagens, elastins, fibronectins, laminins, etc.) that promote tissue-specific remodeling, repair, and regeneration at the site of implantation.[2-3] ECM-based biomaterials are commonly derived from decellularized organs or tissues from various species (e.g., human, porcine, bovine, murine, etc.) in a process that aims at removing immunogenic cellular content while maintaining the integrity of the ECM.[4] The ultimate goal is to produce a bioactive ECM-material that promotes tissue remodeling while lacking immunogenicity and eliminating any adverse host immune reactions.[5-6] ECM scaffolds can be derived from a variety of organs and tissues such as, but not limited to, hearts, vocal folds (vocal cords), lungs, skeletal muscle, pancreas, and dermis with different composition and structure.[4, 7] Even though, the decellularization process is not limited to a particular specie mainly because it can be adjusted depending on the source, porcine is a common model used to develop decellularization protocols. Porcine tissues are readily available given their ubiquitous use for human consumption and represent an abundant source of tissue for the derivation of ECM biomaterials such as, but not limited to, hydrogels.[8] ECM hydrogels can be used both for in vitro cell culture platforms as well as in vivo therapies (e.g., coatings, hybrids, embedded with cells and/or growth factors etc.).

ECM scaffolds are currently used for variety of applications such as implantable or injectable materials, ECM-based bio-inks, and substrates for cell growth.[8-9] Depending on the application, ECM scaffolds can be processed into various formulations such as single sheets, multi-laminated sheets, powders, and hydrogels.[10] Many of these materials are either in preclinical stages or have become commercially available.[11] Patches or sheets derived from skin, small intestine submucosa (SIS), and urinary bladder matrix (UBM) are commonly used for various clinical applications that include, but are not limited to, burn wounds, diabetic ulcers, etc. However, ECM sheets require surgical access when implanted at the wound site and cannot be delivered via minimally invasive techniques.[12]

Current decellularization protocols use prolonged exposure times to each chemical or biological washes that could result in potential disruption of important ECM components leading to a decrease in the inherent bioactivity.[13] Chemical agents (e.g. acids and bases, non-ionic and ionic detergents etc.) and biological agents (e.g. enzymes, chelating agents, etc.) are known to disrupt the ECM ultrastructure and damage important ECM components such as collagens, glycosaminoglycans (GAGs), elastins, and laminin if utilized for extended periods of time.[14] For example, a commonly used decellularization reagent, sodium dodecyl sulfate (SDS), can effectively remove immunogenic cellular and nuclear content (e.g., DNA). However, SDS can affect the overall ultrastructure of the ECM and damage collagens, GAGs, and growth factors.[4] Another example includes sodium deoxycholate, which can disrupt the ECM ultrastructure and remove GAGs.[15] Decellularization reagents are typically put in contact with tissue sheets and subjected to agitation and manual liquid changes. This decellularization approach can result in nonconformities in the homogeneity of the ECM derived-product due to the inherent variability of a manual decellularization process.

Currently, there is no standard decellularization protocol available and each protocol has to be optimized for the specific tissue source, specie, and configuration (sheet vs. whole organ decellularization).[9] Depending on pre- and post-decellularization processing steps, manual-labor, biofabrication method, tissue source, size, thickness etc., the final ECM product may inherently have variable physical and biochemical properties.[16] All these variables can affect the standardization and reproducibility of the final ECM-scaffold.[2] This variability represents a challenge for the scale-up, commercialization, and the translation of ECM-based biomaterials to the clinic and as a cell culture substrate for research. Such deficiencies in the decellularization method provide an opportunity for significant improvement, enabling the harnessing of the full potential of ECM-based biomaterials.

What is needed is a platform that combines new methods and systems to optimize factors such as manufacturing approaches, production costs, production time, and complexity of the manufacturing process, to decrease the amount of time necessary to deliver standardized, high quality, and reproducible ECM materials to the clinic, research laboratories, cosmetic industry, or other fields in a cost-effective manner.[9, 17]

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides an automated tissue decellularization system. In some embodiments, the system comprises a bioreactor; a filtration device, optionally a lateral inline filtration device; a stirring mechanism; a temperature-controlled system, such as a chamber or jacket system, for temperature adjustment and control of the bioreactor, and a fluid control system comprising a dosing system and/or one or more dosing pumps configured to automatically supply one or more reagents to the bioreactor, and/or to apply a feedback for in situ solubilization of ECM for downstream scaffolds production (e.g., hydrogel, matrix-bound vesicles (MBVs), solubilized ECM for bioinks, and the like), and/or remove waste from the bioreactor, wherein the automated decellularization bioreactor system is configured to decellularize a tissue, such as a soft tissue, to produce an extracellular matrix (ECM) scaffold and/or to produce a solubilized downstream ECM-product.

In some embodiments, the bioreactor comprises a series of bioreactors or a plurality of bioreactors. In some embodiments, the filtration device comprises a lateral inline filtration device or a fritted filter.

In some embodiments, the automated decellularization bioreactor system further comprises an in-line spectroscopy-based monitoring system, optionally wherein the in-line monitoring system comprises a spectroscopy-based monitoring system, further optionally wherein the spectroscopy-based monitoring system comprises, but not limited to fluorescence, luminescence, absorbance and/or Raman. In some embodiments, the spectroscopy-based monitoring system is configured to measure nucleic acid removal in the decellularization system, optionally wherein the monitoring is in real-time, optionally wherein the monitoring comprises measurement of an absorbance at 260 nm, 230 nm, 280 nm but not limited to these wavelengths.

In some embodiments, the automated decellularization bioreactor system further comprises a remote dosing controller configured to control the automated tissue decellularization system. In some embodiments, the automated decellularization bioreactor system further comprises a filter component configured to maintain a decellularized tissue within the filtration device while simultaneously allowing the removal of a liquid filtrated phase (e.g. a solubilized ECM-product or waste). In some embodiments, the automated decellularization bioreactor system further comprises a plurality of ports, where the plurality of ports are configured for sampling, effluent removal and/or waste removal, optionally wherein the plurality of ports are configured as a sample port for continuous sampling/monitoring process. In some embodiments, the automated decellularization bioreactor system further comprises a waste removal port positioned on the filtration device. In some embodiments, the automated decellularization bioreactor system further comprises a pump configured to remove waste from the filtration device via the waste removal port and/or a pump configured to manage a feedback system configured for downstream ECM-solubilization and/or to produce a solubilized downstream ECM-product.

In some embodiments, the stirring mechanism comprises one or more magnetic stir bars and a magnetic stir plate and/or wherein the stirring mechanism comprises a rotating filtration system pre-loaded with weights and/or beads, such as sterile weights-beads, optionally, wherein the stirring mechanism further comprises one or more impellers and/or baffles configured to increase turbulence for improved stirring and mixing.

In some embodiments, the dosing system comprises one or more, but not limited to, peristaltic pumps connected in parallel or in series by one or more tubes, wherein the one or more tubes converge on a single input into the inline filtration device. In some embodiments, the one or more dosing pumps are connected to individual reagent reservoirs.

In some embodiments, the reagents are selected from the group comprising enzymatic solutions (e.g., Trypsin), detergents (e.g., Tween-20, Sodium Deoxycholate), alcohols for delipidation (e.g., ethanol), acid or base formulations (e.g., Peracetic Acid), and/or combinations thereof.

In some embodiments, the automated decellularization bioreactor system further comprises a manifold configured to arrange the one or more tubes from the one or more dosing pumps to prevent unwanted interactions between reagents.

In some embodiments, the system is configured to provide adjustability of an exposure time, type of reagent, and/or order in which the tissue is exposed to a reagent.

In some embodiments, the presently disclosed subject matter provides a method of producing extracellular matrix (ECM) based biomaterials or ECM scaffolds. In some embodiments, the method comprises providing an automated decellularization bioreactor system as disclosed herein; performing a size-reducing pre-treating step of a tissue, such as a soft tissue, to increase surface area of the tissue; and processing the pre-treated tissue through the automated decellularization bioreactor system. In some embodiments, the size-reducing pre-treating step comprises grinding, mincing, chopping and/or micronization of the tissue. In some embodiments, the soft tissue comprises heart tissue, vocal fold lamina propria, lung tissue, skeletal muscle tissue, pancreatic tissue, oral mucosa, supraglottic and dermis tissue. In some embodiments, the tissue is provided from different source donors. In some embodiments, the source donors are human, murine, porcine or bovine source donors.

In some embodiments, the method further comprises a series of hypotonic and/or hypertonic short washes and mechanical dissociation of the tissue via stirring.

In some embodiments, processing the tissue through the automated decellularization bioreactor system comprises exposing the tissue to a series of reagents selected from the group comprising enzymatic solutions (e.g., Trypsin), detergents (e.g., Tween-20, Sodium Deoxycholate), alcohols for delipidation (e.g., ethanol), acid or base formulations (e.g., Peracetic Acid), and/or combinations thereof.

In some embodiments, the ECM scaffolds are produced in a reduced time compared to other ECM production methods, and wherein the produced ECM scaffolds maintain cytocompatibility, optionally wherein the produced ECM scaffolds have an overall higher abundance of ECM-related proteins compared to other ECM production methods. In some embodiments, the ECM scaffolds are produced in three hours or less.

In some embodiments, the method comprises scaling up the method and/or pursuing larger ECM-production from tissues, including but not limited to soft tissues.

In some embodiments, the presently disclosed subject matter provides an extracellular matrix (ECM) based biomaterial or ECM scaffold. In some embodiments, the ECM based biomaterial and/or ECM scaffold is produced by a method or system of the presently disclosed subject matter.

In some embodiments, the ECM scaffold comprises a reduced nuclei content compared to a native tissue, optionally a native soft tissue.

In some embodiments, the ECM scaffold comprises a reduced double-stranded DNA (dsDNA) content as compared to a native tissue, optionally a native soft tissue, optionally wherein the ECM scaffold comprises less than about 2 ug dsDNA per mg of dry weight ECM. In some embodiments, the ECM scaffold comprises a higher fibrillar collagens (Types I, II, III, V & XI) content per milligram of dry decellularized ECM compared to classical manual methods, optionally wherein the ECM scaffold comprises larger than about 475 ug of fibrillar collagens (Types I, II, III, V & XI) per mg of dry weight decellularized ECM. In some embodiments, the ECM scaffold comprises proteoglycans, glycoproteins at different abundance as compared to a native tissue, optionally a native soft tissue; or wherein the ECM scaffold comprises increased proteoglycan and glycoproteins as compared to the same tissue decellularized with longer protocols, optionally other ECM derivation methods. In some embodiments, the ECM scaffold comprises increased collagens, keratin, fibrin, and/or other ECM-related proteins as compared to other decellularized ECM from the same tissue type and/or source.

In some embodiments, the ECM scaffold comprises an injectable biomaterial of a particle size according to a filter mesh used within the bioreactor, optionally wherein the particle size is less than about 30 um, less than about 100 um, or less than about 300 um. In some embodiments, the ECM scaffold comprises a biomaterial adapted for aerosolized delivery.

In accordance with some embodiments of the presently disclosed subject matter, a decellularized scaffold end product is provided. In some embodiments, the decellularized scaffold end product comprises a heart tissue or a vocal fold lamina propria (VFLP) or supraglottic (SG), comprising an ECM scaffold as disclosed herein, and having an overall higher abundance of ECM-related proteins compared to other ECM production methods.

Accordingly, it is an object of the presently disclosed subject matter to provide automated approaches for the derivation of acellular extracellular matrix scaffolds from tissues. Objects of the presently disclosed subject matter having been stated above, other objects and advantages of the presently disclosed subject matter will become apparent to those skilled in the art after a study of the following description, Drawings and Examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIG. 1A shows an example of a currently available batch method for the decellularization of porcine heart sheets (sH-ECM) or other soft tissues. In contrast, FIG. 1B is a schematic representation of the disclosed automated decellularization method with a bioreactor connected to automated pumps for the decellularization of porcine micronized heart (mH-ECM or auH-ECM) or other soft tissues.

FIG. 5A is a schematic of the decellularization protocol used to further optimize the dsDNA removal of porcine heart tissue. FIG. 5B is a Box and Whisker plot comparing dsDNA quantification per mg of dry tissue for decellularized mH-ECM and optimized mH-ECM (mH-ECM-O). The optimized decellularization protocol was performed by adjusting the washes, providing evidence that the method can be adapted to different parameters. Three independent decellularizations were performed from each heart, so three individual hearts were tested for a total of 9 samples (n=9). *=P<0.05.). Reference (ref) was set at ~2 μg/mg (for Urinary Bladder Matrix—UBM).

FIG. 6A is a schematic illustration showing that ECM scaffolds (manual and automated) were enzymatically digested and self-assembled into ECM hydrogels; human dermal fibroblasts (HDFn) were seeded on top and cytocompatibility was determined. FIG. 6B is a graph of dsDNA quantification of HDFn cultured on Collagen type I-hydrogel (Col) control, mH-ECMh-O, sH-ECMh, and tissue culture plastic (TCP). *=P<=0.05. Bar graphs represent mean±SEM.

FIG. 7A is a schematic showing the protocol for the automated decellularization of porcine vocal fold lamina propria (mVFLP-ECM). FIG. 7B is a Box and Whisker plot showing dsDNA quantification per mg of dry tissue for native and decellularized sVFLP-ECM and mVFLP-ECM. Approx. 40 VFLPs were combined from 20 different animals and the decellularization was performed three independent times (n=3). *=P<0.05. n.s.=not significant (P>0.05). Reference (ref.) was set at ~2 μg/mg (for Urinary Bladder Matrix—UBM). FIG. 7C is a schematic showing ECM scaffolds were enzymatically digested, self-assembled into ECM hydrogels, and seeded with HDFn for cytocompatibility studies via the LIVE/DEAD assay.

FIG. 12A shows Brightfield microscopy of different automated VFLP-ECM hydrogels filtered with different meshes (FIG. 8). FIG. 12B shows histological sections of the rabbit vocal fold injury model showing the vocal fold with the injection site to the right compared with an untreated vocal fold to the left. The automated VFLP-ECM hydrogel injected was produced with particles lower than 300 μm.

FIG. 14A shows a microscopic view of ECM nebulized collected on a non-tissue culture treated plastic surface. FIG. 14B shows particle size analysis distribution for nebulized ECM collected on a non-tissue culture treated surface. FIG. 14C shows cell attachment test (visible white means cell membrane indication of cell attachment on the surface) indicating ECM delivery via aerosolization.

DETAILED DESCRIPTION

Figures 1A, 1B:
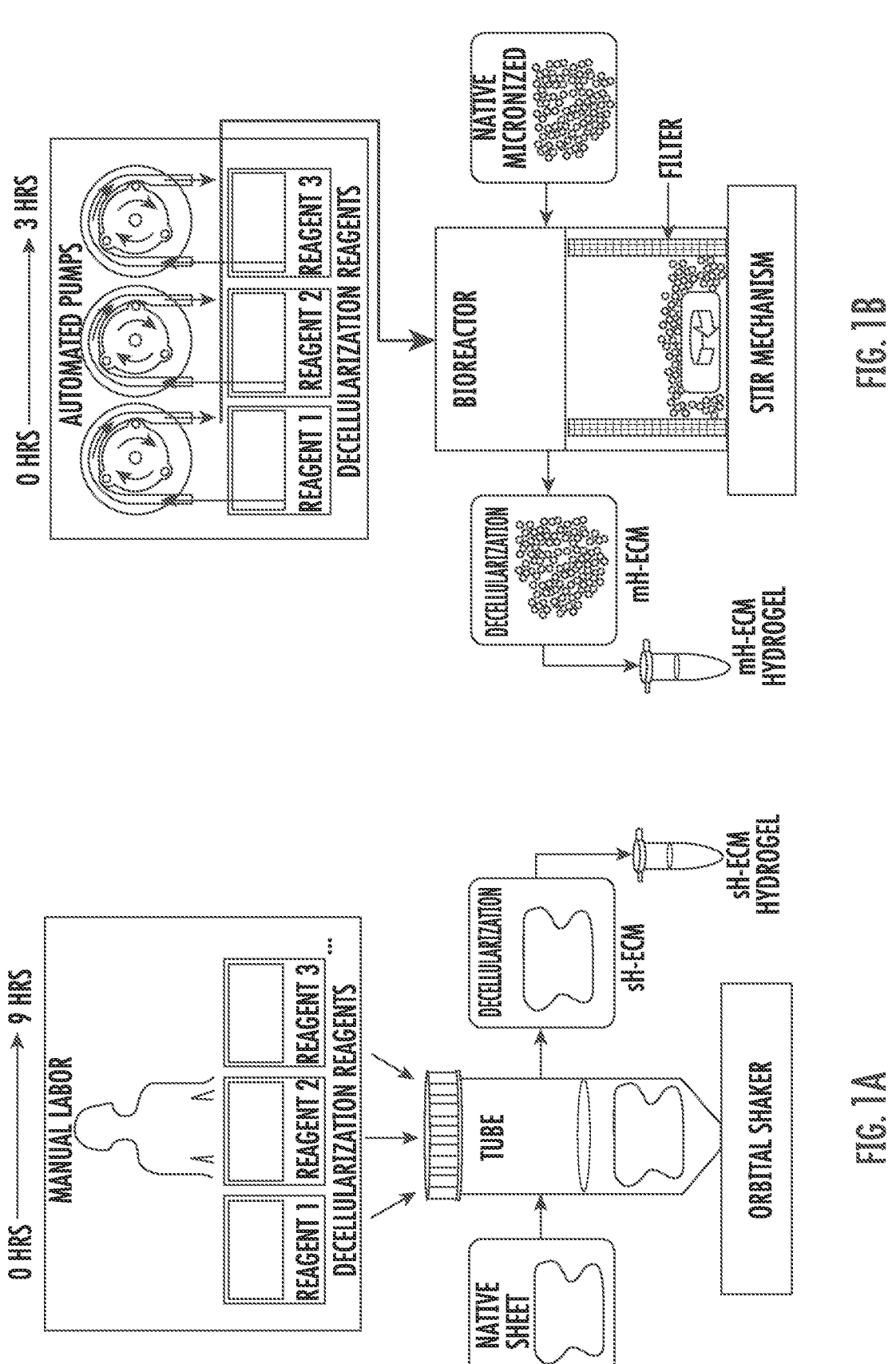
FIGS. 1A-1B include schematic depictions of decellularization systems and methods.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

General Considerations

Provided herein are systems, devices and methods to automate and optimize the decellularization process of representative tissues, such as soft tissues, for ECM-based scaffold production (e.g., solubilized ECM, ECM hydrogels, ECM-Bio inks, among others). Hydrogel, injectable, and inhalable forms of ECM scaffolds are attractive as clinical materials given their ability to elicit constructive remodeling while being amenable to minimally invasive delivery methods.[12] This disclosure is the first to describe a fast, controllable, and automated semi-batch system for the derivation of tissue specific ECM-based biomaterials in a size reduced (e.g., micronized) form for further downstream processing into injectable and/or inhalable ECM biomaterials. The automated decellularization process described here significantly reduces the exposure time to reagents, minimizes lot-to-lot variability, and largely preserves the native composition of the ECM from the decellularized tissue. Additionally, this system is a modular platform that can be adapted to optimize the decellularization process for different soft tissues such as heart, vocal fold lamina propria (VFLP), or supraglottic (SG), but not limited to them. Provided herein is a fast, automated, closed system to derive micronized ECM scaffolds that maintain cytocompatibility and ability to form an injectable hydrogel but can be expanded to other solubilized ECM-scaffolds.

To elaborate, provided herein in some embodiments is a platform comprising: 1) the pre-treatment of the raw material (native tissue) and 2) a closed inline filtration bioreactor system with automated decellularization reagents dosification that enables the production of decellularized extracellular matrix (ECM) scaffolds from native tissue. The platform can be set up in-line to produce different ECMs scaffold products (i.e., solid scaffolds, hydrogels, or matrix-bound vesicles (MBVs) associated with the tissue). The platform was designed considering a closed system to procure the derivation of an aseptic biomaterial for biomedical applications.

No other instrument is currently available that can produce ECM scaffolds for hydrogel production in an automated fashion, significantly reducing the time (up to 3×) of the decellularization process, and capable of reducing the lot-to-lot variation of the acellular ECM product in compliance with quality control parameters. The reduction in time and the automated process were achieved by pre-treating (grounding) the native soft tissue to reduce the size and increase surface area. The inline bioreactor conditions were developed to include the automated change of the decellularization reagents, the elution of the intracellular material such as double stranded DNA (dsDNA), and the retention of the ECM protein content procuring the production of in situ downstream solubilized ECM-scaffolds.

Also, it was discovered that the type of stirring used plays a role for the final quality of the decellularized scaffold. The mechanical stimulation or physical grinding during the process can in some embodiments significantly contribute to the manufacturing of an acellular ECM in compliance with considered quality parameters. The applications for the resultant ECM product range from but not limited to research, cosmetics, clinic, and the biomedical industry field. The decellularization platform is capable of being adjusted to the necessity of the customer regarding the different tissue or donor sources available to produce an ECM scaffold in compliance with the quality parameters considered for the particular application.

Thus, in some embodiments, provided herein is an automated decellularization bioreactor system comprising a lateral inline filtration system/device, a stirring mechanism, and the fluidic system comprising one or more dosing pumps. The pumps are configured to automatically supply one or more reagents to the bioreactor and/or remove waste, samples for in-line monitoring test, or final solubilized ECM-scaffold product from the bioreactor. Such an automated decellularization bioreactor system can be configured to decellularize a soft tissue to produce an extracellular matrix (ECM) scaffold. In some aspects, the automated decellularization bioreactor system can further comprise a filter component configured to maintain the tissue to be decellularized at any stage of the decellularization process within the lateral inline filtration device while simultaneously allowing the removal of filtered liquid phase (e.g., waste). In some aspects, the automated decellularization bioreactor system can further comprise a waste removal port positioned on the lateral inline filtration device. In some aspects, the automated decellularization bioreactor system can further comprise two separate outlet ports connected to two pumps one configured to remove waste and a second one for downstream solubilized ECM-scaffold derivation via feedback to the bioreactor from the lateral inline filtration device.

In some embodiments, the stirring mechanism of the automated decellularization bioreactor system can comprise one or more magnetic stir bars of various shapes and sizes and a magnetic stir plate. However, the stirring mechanisms can be scaled up to an orbital shaker, impellers system, or a lateral rotor filtration system. The one or more dosing pumps can comprise one or more peristaltic pumps connected in parallel or in series by one or more tubes, wherein the one or more tubes converge on a single input into the inline filtration device. The one or more dosing pumps can be connected to individual reagent reservoirs, wherein the reagents are selected from the group comprising but not limited to enzymatic solutions (e.g., Trypsin), detergents (e.g., Tween-20, Sodium Deoxycholate), alcohols for delipidation (e.g., ethanol), acid or base formulations (e.g., Peracetic Acid), and/or combinations thereof. However, any buffer, reagent, or enzymatic solution may be located in the reservoirs and be used as an input for the decellularization protocol to be performed.

In some embodiments, the automated decellularization bioreactor system can further comprise a manifold configured to arrange the one or more tubes from the one or more dosing pumps including washing solutions before and after reagent-feeding to the bioreactor to prevent unwanted interactions between reagents. Such systems can be configured to provide adjustability of an exposure time, type of reagent, and/or order in which the tissue is exposed to a reagent.

Also provided herein are methods of producing extracellular matrix (ECM) scaffolds, comprising performing a size-reducing pre-treating step of a soft tissue to increase surface area of the soft tissue, and processing the pre-treated soft tissue through the automated decellularization bioreactor system as disclosed herein. The size-reducing pre-treating step can comprise micronization of the soft tissue. The soft tissue used in such methods can comprise any soft tissue, including but not limited to heart tissue, vocal fold lamina propria, lung tissue, skeletal muscle tissue, pancreatic tissue, and/or dermis tissue. Such decellularization methods can further comprise a series of hypotonic or hypertonic short washes and mechanical stimulation of the soft tissue via continuous stirring. Processing the soft tissue through the automated decellularization bioreactor system comprises exposing the soft tissue to a series of reagents selected from the group comprising but not limited to enzymatic solutions (e.g., Trypsin), detergents (e.g., Tween-20, Sodium Deoxycholate), alcohols for delipidation (e.g., ethanol), acid or base formulations (e.g., Peracetic Acid), and/or combinations thereof.

In some embodiments, the ECM scaffolds can be produced in a reduced time compared to current manual ECM production methods, and wherein the produced ECM scaffolds maintain cytocompatibility. Notably, in some aspects, the ECM scaffolds are produced in three hours or less.

Also provided herein are extracellular matrix (ECM) scaffolds, including those produced by the disclosed methods and systems. The ECM scaffolds can comprise a reduced nuclei content compared to a native soft tissue. The ECM scaffolds can comprise a reduced double-stranded DNA (dsDNA) content as compared to a native soft tissue, optionally wherein the urinary bladder, optionally porcine urinary bladder matrix (UBM)-ECM (a commercially available ECM-scaffold), comprises around 2 ug dsDNA per mg of dry weight ECM.[21,] The ECM scaffolds can comprise reduced ECM protein composition as compared to a native soft tissue. However, the ECM scaffolds can comprise increased ECM protein composition (e.g., proteoglycans, glycoproteins, keratins, some collagens and/or fibrin) as compared to other decellularized scaffolds derived via longer protocols starting with the same soft tissue.

In accordance with some embodiments of the presently disclosed subject matter, a decellularized scaffold end product is provided. In some embodiments, the decellularized scaffold end product comprises a heart tissue or a vocal fold lamina propria (VFLP) or supraglottic (SG), comprising an ECM scaffold as disclosed herein, and having an overall higher abundance of ECM-related proteins compared to other ECM production methods.

Systems and Methods for Producing ECM Biomaterials and Scaffolds

Figure 2:
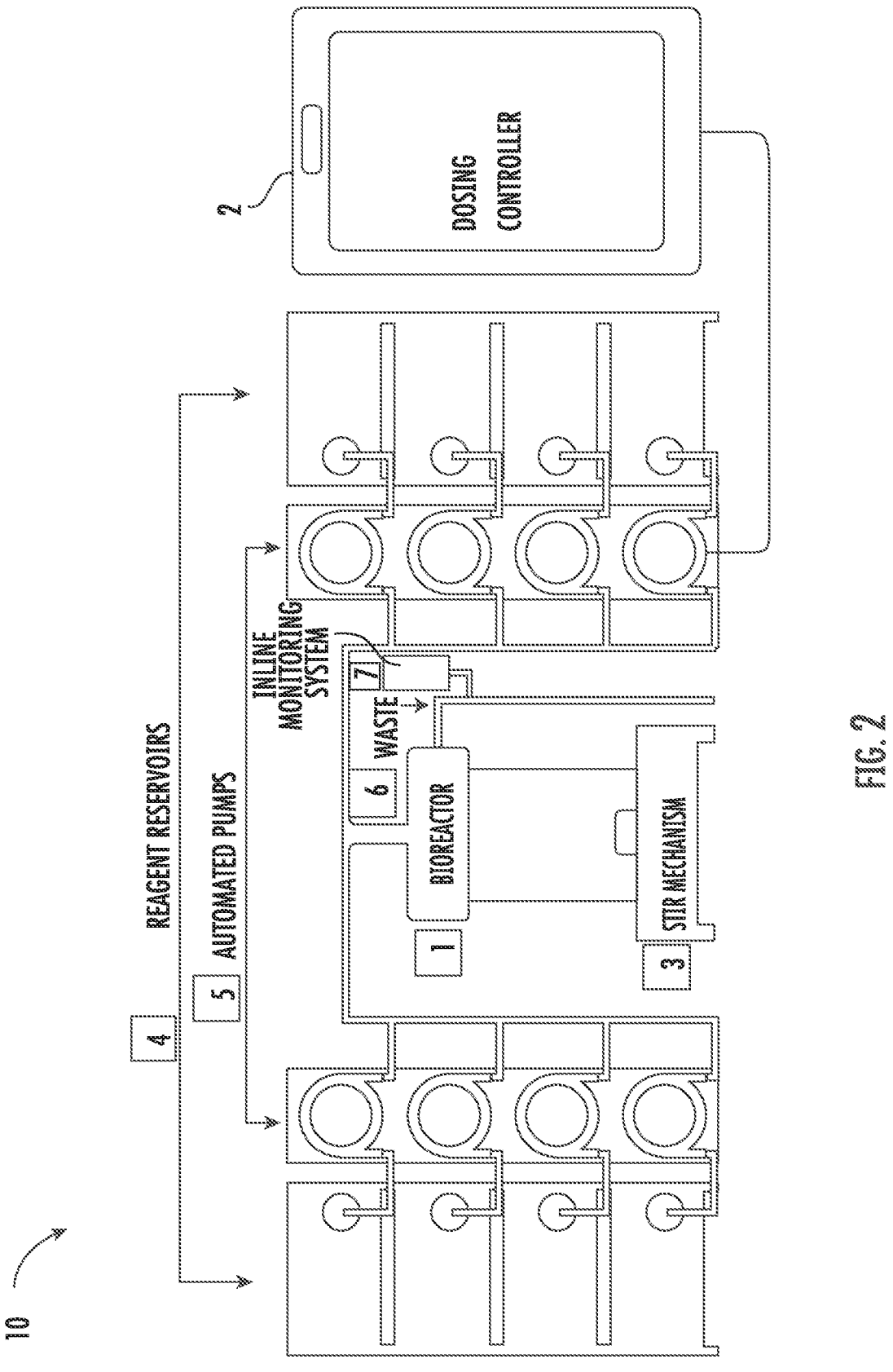
FIG. 2 is a schematic illustration of a bioreactor design of the disclosed systems and methods for automated decellularization.
Figure 9:
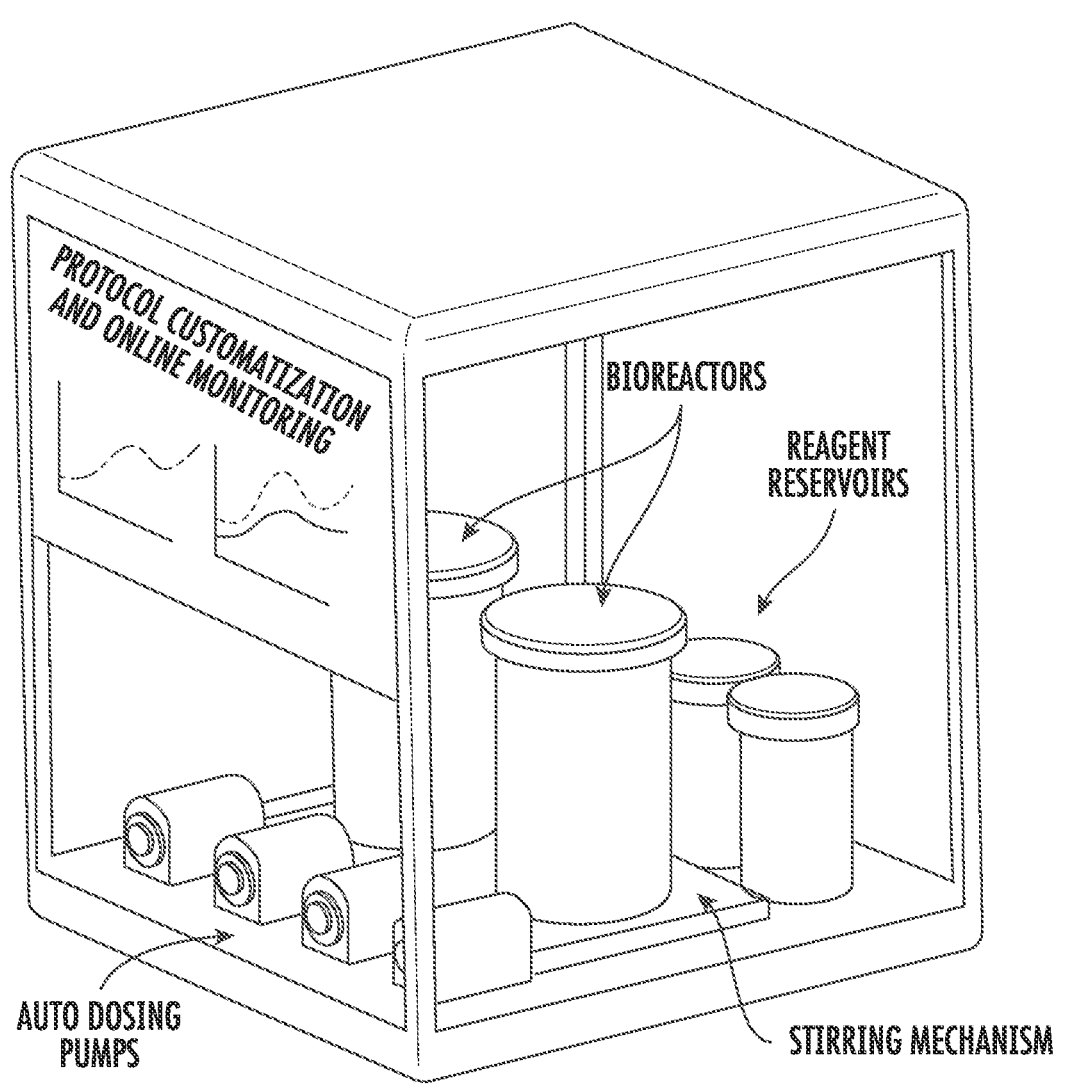
FIG. 9 is a schematic illustration of an embodiment of a single-unit automated decellularization system.

In some embodiments provided herein are automated tissue decellularization systems, the systems 10 comprising a bioreactor 1, a filtration system/device for waste removal 6, optionally a lateral inline filtration device, a stirring mechanism 3, a temperature-controlled system, such as a chamber or jacket system, for temperature adjustment and control of the bioreactor 1, and a fluid control system comprising a dosing system and/or one or more dosing pumps 5 configured to automatically supply one or more reagents from reagent reservoirs 4 to the bioreactor 1, and/or to apply a feedback for in situ solubilization of ECM for downstream scaffolds production (e.g., hydrogel, MBVs, solubilized ECM for bioinks, and the like), and/or remove waste from the bioreactor, as shown in FIG. 2. Such a system 10 can be controlled, locally or remotely, i.e. online, by a dosing controller 2, e.g. a computer. See also FIGS. 1B and 9. Such automated decellularization bioreactor systems can be configured to decellularize a tissue, such as a soft tissue, to produce an extracellular matrix (ECM) scaffold and/or to produce a solubilized downstream ECM-product. Such a bioreactor can comprise a series of bioreactors or a plurality of bioreactors connected in a series. The filtration system/ device can comprise a lateral inline filtration device or a fritted filter. In some embodiments, system 10 comprises an in-line monitoring system 7. In-line monitoring system 7 can comprise an in-line or remote monitoring system, which can be used to evaluate status of the reaction, such as by monitoring the absorbance at 260 nm (Abs. 260 nm) from the bioreactor's effluent (or waste after each decellularization reagent) as a function of the exposure time. See also FIG. 10.

Thus, in some aspects, such automated tissue decellularization systems can further comprise an in-line monitoring tool or system 7, such as but not limited to an in-line spectroscopy-based monitoring tool or system 7. In representative, non-limiting embodiments, the spectroscopy-based monitoring system employs fluorescence, luminescence, absorbance and/or Raman. In some embodiments, the spectroscopy-based monitoring system is configured to measure nucleic acid removal in the decellularization system, optionally wherein the monitoring is in real-time, optionally wherein the monitoring comprises measurement of an absorbance at 260 nm, 230 nm, 280 nm but not limited to these wavelengths.

In some aspects, such automated tissue decellularization systems can further comprise a remote dosing controller configured to control the automated tissue decellularization system. In some aspects, such automated tissue decellularization systems can further comprise a filter component configured to maintain a decellularized tissue within the filtration device while simultaneously allowing the removal of a liquid filtrated phase (e.g. a solubilized ECM-product or waste). In some aspects, such automated tissue decellularization systems can further comprise a plurality of ports, where the plurality of ports are configured for sampling, effluent removal and/or waste removal, optionally wherein the plurality of ports are configured as a sample port for continuous sampling/monitoring process. The automated tissue decellularization systems can further comprise a waste removal port positioned on the filtration device.

In some embodiments, the disclosed automated tissue decellularization systems can further comprise a pump configured to remove waste from the filtration device via the waste removal port and/or a pump configured to manage a feedback system configured for downstream ECM-solubilization and/or to produce a solubilized downstream ECM-product. Moreover, the stirring mechanism can comprise one or more magnetic stir bars and a magnetic stir plate and/or wherein the stirring mechanism comprises a rotating filtration system pre-loaded with weights and/or beads, such as sterile weights-beads, optionally, wherein the stirring mechanism further comprises one or more impellers and/or baffles configured to increase turbulence for improved stirring and mixing or orbital shakers. As will be appreciated by one of ordinary skill in the art, any stirring or agitation mechanism or device can be used so long as it provides adequate mechanical stirring and/or agitation.

The dosing system can comprise one or more pumps, such as but not limited to peristaltic pumps, connected in parallel or in series by one or more tubes, wherein the one or more tubes converge on a single input into the inline filtration device. Indeed, any suitable pump or other dosing device, or combination of pumps and/or other dosing device, as would be apparent to one of ordinary skill in the art upon a review of the instant disclosure, can be employed. The one or more dosing pumps can be connected to individual reagent reservoirs. In some embodiments, the reagents can be selected from the group comprising but not limited to enzymatic solutions (e.g., Trypsin), detergents (e.g., Tween-20, Sodium Deoxycholate), alcohols for delipidation (e.g., ethanol), acid or base formulations (e.g., Peracetic Acid), and/or combinations thereof. In some aspects, such automated tissue decellularization systems can further comprise a manifold configured to arrange the one or more tubes from the one or more dosing pumps to prevent unwanted interactions between reagents. The system can be configured to provide adjustability of an exposure time, type of reagent, and/or order in which the tissue is exposed to a reagent.

Methods of producing extracellular matrix (ECM) based biomaterials or ECM scaffolds are also provided herein. Such methods can comprise performing a size-reducing pre-treating step of a tissue, such as a soft tissue, to increase surface area of the tissue, and processing the pre-treated tissue through the automated decellularization bioreactor system. The size-reducing pre-treating step comprises, but is not limited to, grinding, mincing, chopping and/or micronization of the tissue. By way of example and not limitation, the soft tissue can comprise heart tissue, vocal fold lamina propria, lung tissue, skeletal muscle tissue, pancreatic tissue, oral mucosa, supraglottic and dermis tissue. In some embodiments, the tissue is provided from different source donors. In some embodiments, the source donors are human, murine, porcine or bovine source donors.

The methods can further comprise a series of hypotonic and/or hypertonic short washes and mechanical dissociation of the tissue via stirring. A stirring mechanism or device can be used as described herein.

In some embodiments, processing the tissue through the automated decellularization bioreactor system can comprise exposing the tissue to a series of reagents selected from the group comprising but not limited to enzymatic solutions (e.g., Trypsin), detergents (e.g., Tween-20, Sodium Deoxycholate), alcohols for delipidation (e.g., ethanol), acid or base formulations (e.g., Peracetic Acid), and/or combinations thereof.

Notably, by using the disclosed systems, devices and methods, the ECM scaffolds can be produced in a reduced time compared to other ECM production methods, and wherein the produced ECM scaffolds maintain cytocompatibility, optionally wherein the produced ECM scaffolds have an overall higher abundance of ECM-related proteins compared to other ECM production methods. For example, the ECM scaffolds can be produced in three hours or less, in some embodiments in about 3 hours, about 2 hours, or about 1 hour. Based on the nature of the disclosed systems the methods can be scaled up such that larger ECM-production from soft tissue can be achieved.

Using the disclosed systems and methods, also provided herein are extracellular matrix (ECM) based biomaterial or ECM scaffolds. The ECM scaffolds can comprise a reduced nuclei content compared to a native tissue, optionally a native soft tissue. By way of example and not limitation, the ECM scaffold can comprise a reduced double-stranded DNA (dsDNA) content as compared to a native tissue, optionally a native soft tissue. As an example, the ECM scaffold can comprise less than about 2 ug dsDNA per mg of dry weight ECM, or less than about 2 ug dsDNA/mg, less than about 1.5 ug dsDNA/mg, less than about 1 ug dsDNA/mg, less than about 0.5 ug dsDNA/mg.

Figure 13:
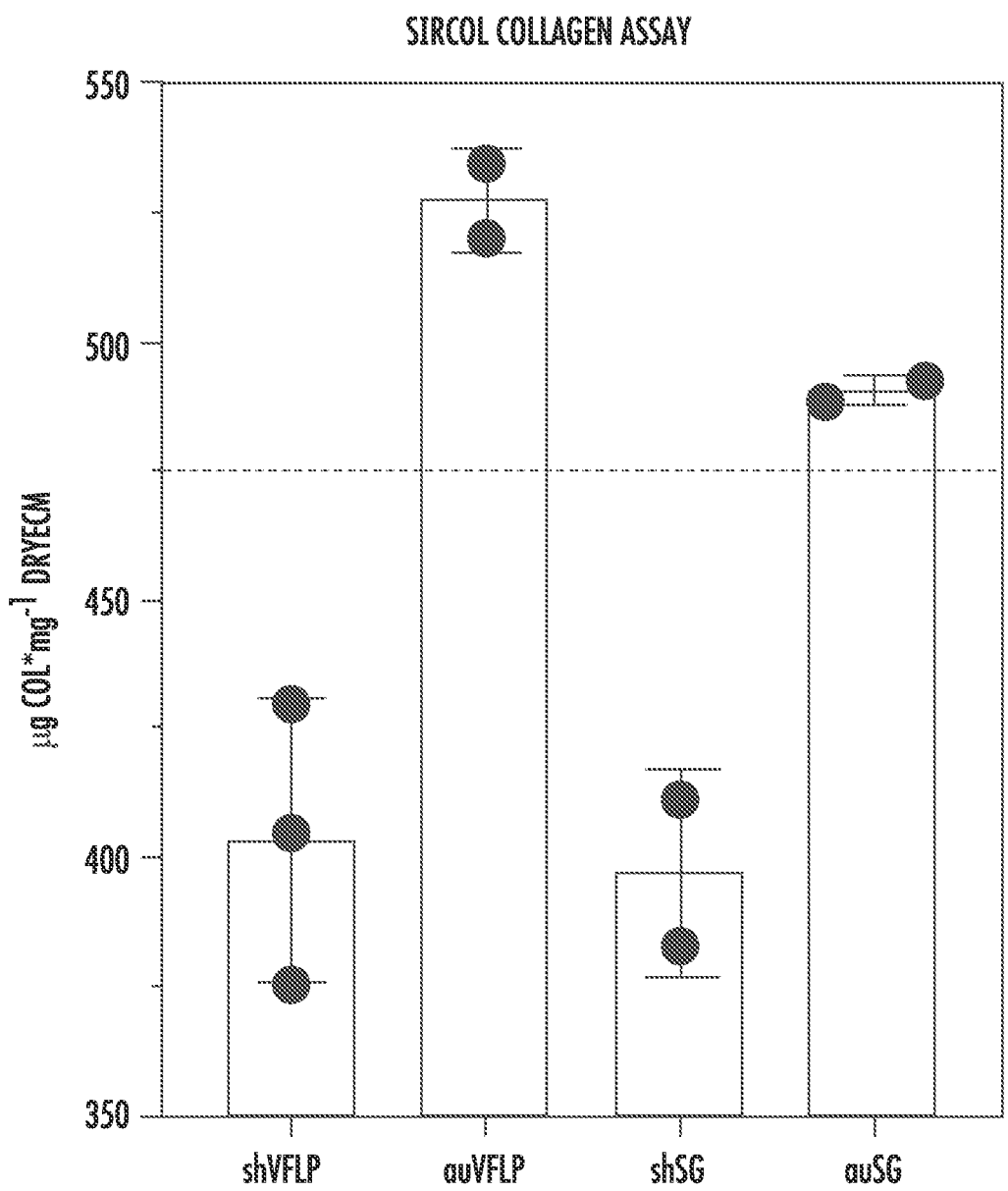
FIG. 13 is a graph of the results of a Sircol collagen assay (sh=sheet, au=automated, VFLP=vocal fold lamina propria, SG=supraglottic). The Sircol collagen assay was used to detect the amount of fibrillar collagens (Types I, II, III, IV, and XI) in the manual sheet vs. automated method for VFLP and SG.

In some embodiments, the ECM scaffold can comprise a higher fibrillar collagens (Types I, II, III, V & XI) content per milligram of dry decellularized ECM compared to classical manual methods. By way of example and not limitation and referring to FIG. 13, such ECM scaffolds can comprise greater than about 475 ug of fibrillar collagens (Types I, II, III, V & XI) per mg of dry weight decellularized ECM, or more than about 475 ug of fibrillar collagens (Types I, II, III, V & XI) per mg, more than about 500 ug of fibrillar collagens (Types I, II, III, V & XI) per mg, more than about 525 ug of fibrillar collagens (Types I, II, III, V & XI) per mg, or more than about 550 ug of fibrillar collagens (Types I, II, III, V & XI) per mg. See also Table 1 below.

TABLE 1

| Difference in collagen protein composition automated VFLP-ECM vs manual VFLP-ECM | | | |
| --- | --- | --- | --- |
| Protein | Gene ID Sub units | Log2 FC (LFQ automatedVFLP – LFQ manualVFLP) | Statistical significance |
| Collagen I | COL1A1 | 2.57 | * |
| | COL1A2 | 3.88 | * |
| Collagen II | COL2A1 | 3.9 | * |
| Collagen III | COL3A1 | 2.82 | * |
| Collagen IV | COL4A1 | −0.67 | ns |
| | COL4A2 | 0.6 | ns |
| | COL4A3 | −0.29 | ns |
| | COL4A5 | 0.36 | ns |
| Collagen V | COL5A2 | 2.88 | ns |
| | COL5A3 | 1.37 | ns |
| Collagen VI | COL6A1 | 0.3 | * |
| | COL6A2 | 1.18 | ns |
| | COL6A3 | 1.91 | * |
| | COL6A5 | 2.78 | ns |
| | COL6A6 | 1.8 | ns |
| Collagen VII | COL7A1 | 1.21 | ns |
| Collagen VIII | COL8A1 | 2.54 | ns |
| Collagen IX | COL9A1 | 6.64 | * |
| | COL9A3 | 6.64 | * |
| Collagen XI | COL11A1 | −1.78 | ns |
| Collagen XII | COL12A1 | −0.37 | ns |
| Collagen XIV | COL14A1 | −2.15 | ns |
| Collagen XVIII | COL18A1 | −0.21 | ns |
| Collagen XXI | COL21A1 | 1.38 | ns |

Log2 FC = Logarithm base 2,
FC = Fold change
LFQ = Label free quantification
"–" values = less abundance in automated_VFLP 5
* = p-values < 0.05
ns = no-significance In some embodiments, the ECM scaffolds and biomaterials can comprise proteoglycans, glycoproteins at different abundance as compared to a native tissue, optionally a native soft tissue. Additionally, the ECM scaffolds can comprise increased proteoglycan and glycoproteins as compared to the same tissue decellularized with longer protocols, optionally other ECM derivation methods. In some aspects, the ECM scaffolds and biomaterials can comprise increased keratin, collagens, fibrin, and/or other ECM-related proteins as compared to other decellularized ECM from the same tissue type and/or source.

Notably, the ECM scaffolds and biomaterials provided herein can comprise or be in the form of an injectable biomaterial of a particle size according to a filter mesh used within the bioreactor, optionally wherein the particle size is less than about 30 um, less than about 100 um, or less than about 300 um.

In some embodiments, the ECM scaffolds and biomaterials provided herein can comprise or be in the form of a biomaterial suitable for aerosolization, e.g., an inhalable biomaterial. In some embodiments, the presently disclosed subject matter provides for ECM aerosolization, which can, for example, involve processing the solid-ECM into particles no larger than 15 μm to target the respiratory system, including the upper respiratory system, by suspending the solid particles into a solution, such as but not limited to a solution comprising a physiologically acceptable carrier (such as a buffer), to be nebulized. In some embodiments, the presently disclosed subject matter provides for an aerosolization method by using the digested but pre-gel form of the ECM. By way of example and not limitation, the solubilized-ECM is diluted in an acidic condition to a desired concentration, such as to 0.5 mg/mL, using a diluent such as deionized water. The ECM-solution is then neutralized and filtered using a 15 μm strainer. The ECM solution can be further diluted to a desired working concentration, such as about 125 μmg/mL in a buffer, such as a phosphate buffer, for aerosolization. The solution can be nebulized using a mesh nebulizer or other suitable nebulizer as would be apparent to one of ordinary skill in the art upon a review of the instant disclosure. It is further noted that ECM from vocal fold lamina propria provides modulatory properties in fibroblasts and macrophages. Representative, non-limiting examples of therapeutic applications include fibrosis in the lungs and fibrosis of the vocal folds.

Definitions and General Considerations

Unless otherwise defined, all technical and scientific terms used herein have the same meaning as commonly understood by one of ordinary skill in the art to which this presently disclosed subject matter belongs. The terminology used in the description of the presently disclosed subject matter herein is for the purpose of describing particular embodiments only and is not intended to be limiting of the presently disclosed subject matter.

All publications, patent applications, patents, and other references cited herein are incorporated by reference in their entireties for the teachings relevant to the sentence and/or paragraph in which the reference is presented.

List of Abbreviations:
  ECM Extracellular Matrix
  Col Type I Collagen
  TCP Tissue Culture Plastic
  sH-ECM sheet Heart-Extracellular Matrix
  sH-ECMh sheet Heart-Extracellular Matrix hydrogel
  mH-ECM micronized Heart-Extracellular Matrix
  mH-ECM-O micronized Heart-Extracellular Matrix Optimized
  mH-ECMh-O micronized Heart-Extracellular Matrix hydrogel Optimized
  sVFLP-ECM sheet Vocal Fold Lamina Propria-Extracellular Matrix
  sVFLP-ECMh sheet Vocal Fold Lamina Propria-Extracellular Matrix hydrogel
  mVFLP-ECM micronized Vocal Fold Lamina Propria-Extracellular Matrix
  mVFLP-ECMh micronized Vocal Fold Lamina Propria-Extracellular Matrix hydrogel
  auVFLP-ECM automated Vocal Fold Lamina Propria-Extracellular Matrix
  auSG-ECM automated Supraglottic-Extracellular Matrix
Note: mVFLP-ECM and auVFLP-ECM refer to the same type of automated derived biomaterial.

Unless the context indicates otherwise, it is specifically intended that the various features of the presently disclosed subject matter described herein can be used in any combination. Moreover, the presently disclosed subject matter also contemplates that in some embodiments of the presently disclosed subject matter, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Like numbers refer to like elements throughout. In the figures, the thickness of certain lines, layers, components, elements or features can be exaggerated for clarity. Where used, broken lines illustrate optional features or operations unless specified otherwise.

As used in the description of the presently disclosed subject matter and the appended claims, the singular forms "a," "an" and "the" are intended to include the plural forms as well, unless the context clearly indicates otherwise.

Also, as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value can include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "under," "below," "lower," "over," "upper" and the like, can be used herein for ease of description to describe an element's or feature's relationship to another element(s) or feature(s) as illustrated in the figures.

It will be understood that, although the terms first, second, etc., can be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the presently disclosed subject matter. The sequence of operations (or steps) is not limited to the order presented in the claims or figures unless specifically indicated otherwise.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

The presently disclosed subject matter will now be described with reference to the following examples. It should be appreciated that these examples are not intended to limit the scope of the claims to the presently disclosed subject matter, but are rather intended to be exemplary of certain embodiments. Any variations in the exemplified methods that occur to the skilled artisan are intended to fall within the scope of the presently disclosed subject matter.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Materials and Methods Used in Examples 1-6

Tissue Decellularization
Tissue Dissection and Decellularization (Control/Manual Method)
Heart Decellularization Case Three porcine heart dissections and decellularizations were performed as previously described.[18] Briefly, porcine hearts (Nahunta Pork Outlet, Raleigh, N.C.) were procured from market weight pigs, thoroughly cleaned of excess connective tissue, blood, and debris, and frozen at −80° C. for at least 24 hours. The frozen heart was sliced into thin (2-3 mm) sheets (sH) using a commercially available meat slicer. Random slices from throughout the entire porcine heart were selected for the manual decellularization method. The remaining portions of the heart were randomized, micronized, and collected in order to obtain a more uniform sample to be decellularized as described in Automated 3-hour Tissue Decellularization Protocol section. Next, the sheets were placed in 50 mL tubes and treated with the following solutions under constant agitation on an orbital shaker: deionized (DI) water for 5 minutes, 2× Dulbecco's Phosphate-Buffered Saline (DPBS) (GeneClone, Raleigh, N.C.) for 15 minutes, 0.02% trypsin (Life Technologies, Carlsbad, Calif.) for 2 hours, DI water for 5 minutes, 2× DPBS for 15 minutes, 3% v/v Tween-20 (Sigma-Aldrich, St.

Louis, Mo.) for 2 hours, DI water for 5 minutes, 2× DPBS for 15 minutes, 4% w/v sodium deoxycholate (Sigma-Aldrich) for 2 hours, DI water for 5 minutes, 2× DPBS for 15 minutes, 0.1% v/v peracetic acid (Sigma-Aldrich) in 4% v/v ethanol solution for 1 hour, 1× DPBS for 5 minutes, DI water for 5 minutes, and 1× DPBS for 15 minutes. The decellularized heart sheets (sH-ECM) were stored in 1× DPBS with 1% penicillin/streptomycin (Life Technologies) at 4° C. Three independent decellularizations were performed from each heart, so three individual hearts were tested for a total of 9 samples (n=9).

Vocal Fold Lamina Propria Decellularization Case

Porcine VFLP dissection and decellularization were performed as previously described.[19] Porcine larynges (Nahunta Pork Outlet, Raleigh, NC) were dissected and the VFLP of each of the true vocal folds was cleaned from surrounding connective tissue and frozen at −80° C. for at least 24 hours. A biological pool of 40 VFLPs were combined from 20 different animals. Half of the batch was used for the manual decellularization, which was performed three independent times (n=3) of 7, 7, and 6 VFLP tissues respectively. The VFLPs were treated with the following solutions under constant agitation on an orbital shaker: three times with 1× DPBS for 15 minutes each, 4% sodium deoxycholate w/v (Sigma-Aldrich, St. Louis, MO) for 2 hours, 1× DPBS for 15 minutes, deoxyribonuclease (DNase) I (Sigma-Aldrich) at 273 Kunitz/mL in PBS pH 7.4 supplemented with 2.5 mM $Mg^{2+}$ and 0.1 mM $Ca^{2+}$ for 2 hours, 1× DPBS for 15 minutes, 0.1% v/v peracetic acid (Sigma-Aldrich) in 4% v/v ethanol solution for 30 minutes, 1× DPBS for 15 minutes. The decellularized VFLPs (sVFLP-ECM) were stored in lx DPBS with 1% penicillin/streptomycin (Life Technologies, Carlsbad, CA) at 4° C.

Automated 3-Hour Tissue Decellularization Protocol

The remaining heart pieces from the control method were immediately cut into thick slices and micronized using a meat grinder (Altra Model AZ-MG090, Foshan, Guangdong, China). Three independent decellularizations were performed from each heart, so three individual hearts were tested for a total of 9 samples (n=9). Meanwhile, half of the dissected pool of the VFLP batch (20 VFLPs) were ground after freezing overnight using a Ninj a Blender® (Amazon, Seattle, WA). At least three independent decellularizations were performed (n=3). The micronized tissues were then placed in a custom-made bioreactor (described in Bioreactor Setup section) and treated with the solutions listed in Table 2 (heart) or Table 4 (VFLP) under constant stirring. The decellularized micronized scaffold (mH-ECM or mVFLP-ECM) was lyophilized overnight and stored at room temperature.

Bioreactor Setup

The bioreactor comprises modular components to allow for continuous decellularization. An inline mesh filter (Bouncer, Wilmington, NC) and screen (Bouncer) were used to form the body of the bioreactor, where the mesh filter size can be adjusted depending on the particle size distribution after tissue grinding. To ensure consistent interaction between the tissue samples and reagents, mechanical stirring of the system was accomplished using magnetic stir bars (Fisher Scientific) placed at the center of the bioreactor. The bioreactor was placed on top of a magnetic stirrer; however, other stirring methods such as, but not limited to, orbital shakers can be used. Programmable auto dosing pumps (Jebao, Guangdong, China) were used to load the reagents into the bioreactor input by connecting 8 mm silicone tubing (Uxcell, Hong Kong, China) and T shaped three-way valves (Uxcell) to the main 8 mm input tube. The number of active auto dosing pumps was adaptable to the decellularization protocol used. Finally, waste was removed by feeding an 8 mm silicone tube (Uxcell) through the outlet to the bottom of the system. The waste was pumped to an external waste tank. A more detailed description is found in Example 2.

Histological Analysis

Tissue samples of native and decellularized sH-ECM and mH-ECM were fixed in 4% formaldehyde (Sigma-Aldrich) overnight and stored in 70% ethanol. The samples were trimmed and sectioned at a thickness of 5 μm and subjected to Hematoxylin and Eosin (H&E) staining for nuclei removal comparison before and after decellularization with both protocols (i.e., automated and manual). The histological staining was performed at the Histology Laboratory in the College of Veterinary Medicine at North Carolina State University.

Double Stranded DNA (dsDNA) Quantification

Native heart and VFLP tissues and decellularized ECM scaffolds were lyophilized overnight. Afterwards, ~3 mg per sample was taken and digested in 20 μL (at 20 mg/mL) Proteinase K Solution (Qiagen) and 180 μL Buffer ATL (Qiagen) overnight at 60° C. Meanwhile, for the cells cultured on the ECM hydrogels, three hydrogel replicates of 100 μL/each were collected and digested using the same ratio of Proteinase K/ATL buffer.

dsDNA quantification was performed using the QuantiFluor® dsDNA System (Promega, Madison, Wis.) according to the manufacturer's instructions. The digested samples were diluted and mixed thoroughly using 800 uL of TE pH 7.4 buffer (ThermoFisher Scientific). Then, a second dilution (1:50) was prepared using the same buffer. Further dilutions were required for native samples to reach a signal in the same threshold as the standards supplied by the kit. The samples were read using an Infinite M200 Pro plate reader (Tecan Mannedorf, Switzerland).

Discovery Proteomics for mH-ECM (Automated) vs. sH-ECM (Manual)

Discovery proteomic strategies were used to characterize and compare the overall protein composition and abundance of decellularized sH-ECM and mH-ECM scaffolds.

Sample Preparation

Three porcine hearts were used to produce three independent decellularized mH-ECM or sH-ECM scaffolds. Then, to generate a biological representative sample, 10 mg each of mH-ECM or sH-ECM were pooled into a final 30 mg sample per condition. The samples were suspended in 1 mL of 50 mM ammonium bicarbonate (pH 8.0) with 5% Sodium Deoxycholate (SDC) for digestion, homogenization, and determination of their protein concentration using bicinchoninic acid assay (BCA assay). Samples were prepared prior to injection into the mass spectrometry (MS) system by using a filter-aided sample preparation (FASP) approach.[20]

Liquid Chromatography (LC)

All samples were processed according to a discovery proteomics workflow using an Easy Nano-LC 1200 complexed to a Thermo Scientific Q-Exactive HFX with an EASY-Spray source for acquisition. A Thermo Scientific Acclaim™ PepMap™ 100 trap column (C18 LC Columns, 3 μm particle size, 75 μm ID, 20 mm length (164946)) was utilized in-line with an EASY-Spray™ analytical column (2 μm particle size, 75 μm ID, 250 mm length (ES802A), at 35° C.).

Data Analysis

Raw data was loaded into Proteome Discoverer 2.4.0.305 (ThermoFisher Scientific) for analysis. A label-free quantitation (LFQ) workflow was used. For peptide searching, protein FASTA database was downloaded via Proteome Discoverer from SwissProt (fully annotated) and TrEMBL (unreviewed proteins) databases for Sus Scrofa (taxonomy ID=9823). A max of 8 equal mods and a max of 3 total dynamic mods were used per peptide. The following post translational modifications (PTMs) were accommodated in the search algorithm (modified amino acids in parentheses): oxidation (K, M, P), deamidation (N, Q), galactosyl (K), Glucosylgalactosyl (K), and Lys→Allysine (K).

Hydrogel Preparation

ECM scaffolds were frozen in liquid nitrogen, powdered using a mortar and pestle, and lyophilized overnight. The lyophilized ECM was digested to obtain a solution of 10 mg/mL at a ratio of 10:0.6:1 of H-ECM, pepsin (3200-4500 units/mg; Sigma-Aldrich), and 0.1 M HCl (Sigma-Aldrich) on a magnetic stir plate at room temperature for 48 hours. The resulting ECM digestion was aliquoted and stored at −20° C. until use. ECM hydrogels (mH-ECM, sH-ECM, mVFLP-ECM, sVFLP-ECM; 6 mg/mL) were prepared by thawing the ECM digestion, adjusting its pH to 7.3±0.2 using 0.1 M NaOH (Sigma-Aldrich), and balancing the salt content using 10× DPBS and 1× DPBS. FibriCol I, Collagen Type I>97% (Advanced Biomatrix, Carlsbad, CA) was used as a collagen control (Col). Next, 250 µL of the ECM hydrogels or Col control were pipetted into each well of a 24-well plate (Corning, NY). Crosslinking into a gel was achieved by placing the plate in the incubator at 37° C. for 30-45 minutes.

Cell Culture Conditions

Primary human dermal fibroblast normal cells (HDFn) were purchased from ATCC® (Manassas, VA). HDFn were cultured in tissue culture plastic flasks (VWR, Radnor, PA) using Dulbecco's Modified Eagle Medium (DMEM) (Life Technologies) supplemented with 10% fetal bovine serum heat-inactivated (Genesee Scientific, San Diego, CA) and 1% penicillin/streptomycin. Media was changed every 3 days. HDFn cell passages 10-18 were used for this study. HDFn were passed when reaching 80-90% confluency by incubation with 0.05% trypsin-EDTA (Life Technologies) for 5 minutes and seeded onto tissue culture plastic flasks.

LIVE/DEAD Viability Assay

HDFn cells were seeded on top of the hydrogels produced with Col, sH-ECM, mH-ECM, sVFLP-ECM, and mVFLP-ECM (40,000 cells/condition). The hydrogels seeded with HDFn were stained at 24 and 48 hours using the LIVE/DEAD Viability/Cytotoxicity Kit (Life Technologies) according to the manufacturer's instructions. The samples were imaged using bright field and fluorescence microscopy (Revolve microscope, Echo, San Diego, CA).

Statistical Analysis

Statistical analysis was performed using GraphPad PRISM 8.0 software. All experiments were performed at least three independent times unless otherwise noted. Proteomic discovery analysis was performed using ThermoFisher Proteome Discoverer 2.4. The hypothesis test was ANOVA (individual proteins). Student unpaired t-test with Welch's correction was performed for dsDNA quantification analysis. A value of $P<0.05$ was considered significant unless otherwise noted.

Example 1

Fast Automated Decellularization Approach

Manual labor is a factor that contributes to lot-to-lot variation and represents a challenge to a scalable and continuous manufacturing process. Additionally, the variety of decellularization protocols and the labor-intensive aspect hinder the standardization of the process. FIG. 1B provides a schematic of the overall experimental approach using the novel systems and methods disclosed herein, particularly as compared to existing techniques (FIG. 1A).

As shown in FIG. 1A, one of the current methods for the decellularization of porcine heart sheets requires about 9 hours for completion. In this case, each reagent is manually fed in a batch reaction configuration.[18] The method starts with a thin sheet of heart (sH) placed inside a container and sequentially exposed to different decellularization reagents. It is important to highlight that the homogeneity and thickness (2-3 mm) of the tissue impacts the success of the decellularization process. These factors affect the penetration and effectiveness of the decellularization reagents. Since this method is dependent on manual labor, variations in the end product are frequent and often unavoidable.

The new automated system is illustrated in FIG. 1B and involves a size reduction pre-treatment of the native soft-tissue (i.e., micronization), a custom-adapted inline filtration bioreactor connected to automated dosing pumps allowing a semi-batch reactor setting. The system can produce decellularized porcine heart ECM in approximately 3 hours. The automated approach starts with a pre-treatment of the tissue via micronization to reduce size and increase surface area procuring to reduce the exposure times required for each decellularization reagent. The settings used can be adjusted to further optimize the decellularization protocol as this platform allows for changes in the exposure time, the type of reagent, and the order in which the tissue is exposed to a reagent. In addition, the platform can be tailored to decellularize other soft tissues from different sources and species.

Example 2

Platform Design

FIG. 2 shows a schematic of a representative embodiment of the automated decellularization system. We have identified that vertical filtration resulted in clogging of the system due to the nature of soft tissues. Therefore, a lateral inline filtration system was utilized. The stirring was a requirement to ensure a homogenous decellularization environment and mechanically stimulate the tissue. The semi-batch system can be connected to various dosing pumps in order to automate the reagent addition and waste removal.

The micronized native tissue was resuspended in DI water and transferred by pipetting into the bioreactor (1) through the top inlet. By way of example, but not limitation, such a bioreactor can have a 178-µm mesh filter placed inside. Different filter sizes can be used depending on the size of the pretreated native tissue. By way of example, but not limitation, such bioreactor can have a (2) dosing controller for the fluidic system. The filter is used to retain the decellularized tissue within the bioreactor while allowing the removal of the liquid filtrated phase (e.g., waste) during the process. The liquid phase is removed from the bottom of the system through a tube that is placed outside of the filter and connected through the output of the bioreactor lid. Stirring mechanism (3), e.g. a stir plate with stir bars, or other suitable stirring apparatus, provides stirring and mechanical stimulation inside the bioreactor. Individual peristaltic pump (5) outputs were connected in parallel (but could also be connected in series) by tubes that are joined through connectors that converge on the input of the bioreactor lid. The pump inputs are then connected to individual reagent reservoirs (4). An additional peristaltic pump was used to pump the liquid filtrated phase (e.g., waste) from the bioreactor to the designated reservoir (e.g., waste tank (6)). By way of example, but not limitation, such bioreactor can have an (7) in-line monitoring system tracking the decellularization advancement via spectroscopy measurements of the bioreactor effluent (e.g., absorbance, Raman, fluorescence, or luminescence). The feeding lines from the pump outlets were connected in the manifold prior to the bioreactor input and arranged to prevent unwanted interactions between reagents. In addition, the pumps responsible for DPBS and DI water washes were located at the distal end of the manifold to allow for clearing of any residual decellularization reagents in the tubing. At the scale worked, the pumps were programmed to deliver 30 mL of each reagent and remove waste at designated time points. Finally, the bioreactor is placed on a magnetic stir plate (3) and set between 200-500 RPM. Following decellularization, the samples were characterized to evaluate the efficacy of the process.

In some embodiments, system 10 comprises an in-line monitoring system 7. In-line monitoring system 7 can comprise an in-line or remote monitoring system, which can be used to evaluate status of the reaction, such as by monitoring the absorbance at 260 nm (Abs. 260 nm) from the bioreactor's effluent (or waste after each decellularization reagent) as a function of the exposure time. See also FIG. 10.

Figure 8:
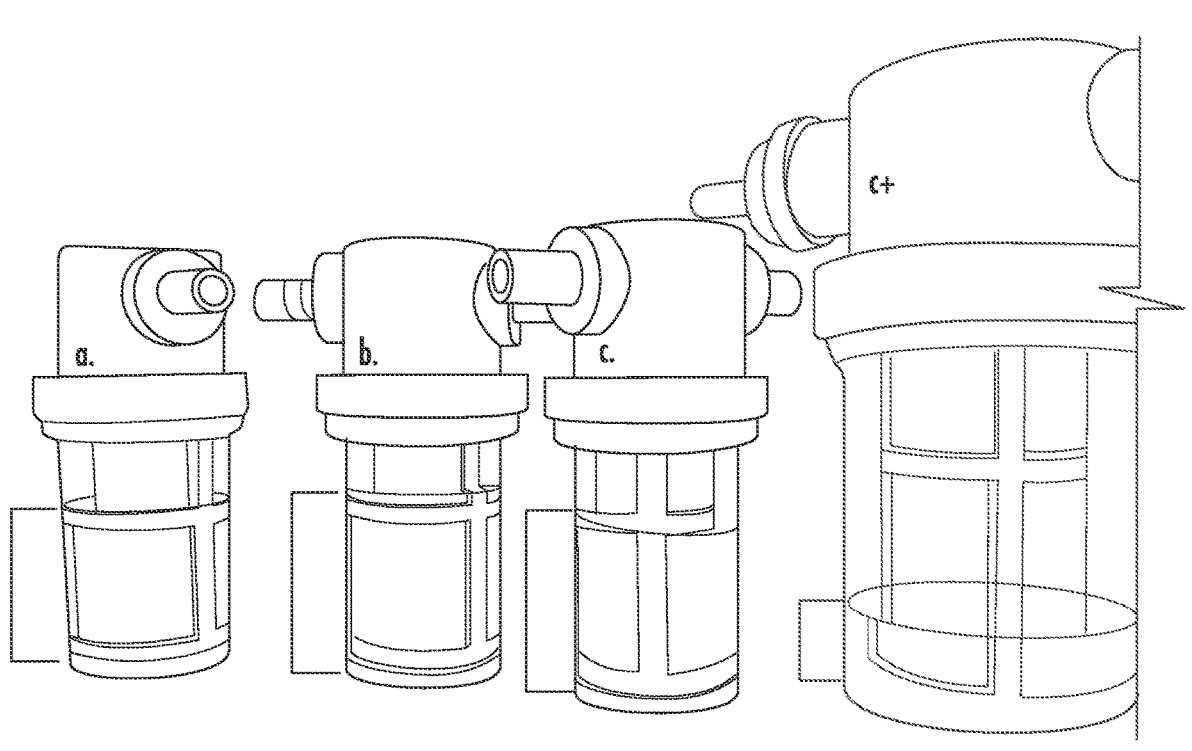
FIG. 8 is an image of different volumes of solubilized ECM (pre-hydrogel form) within a bioreactor using different filter pore sizes (a.=178 μm, b.=304 μm, c., and c+=915 μm); the volume level of solubilized ECM is marked with the brackets.
Figure 12A:
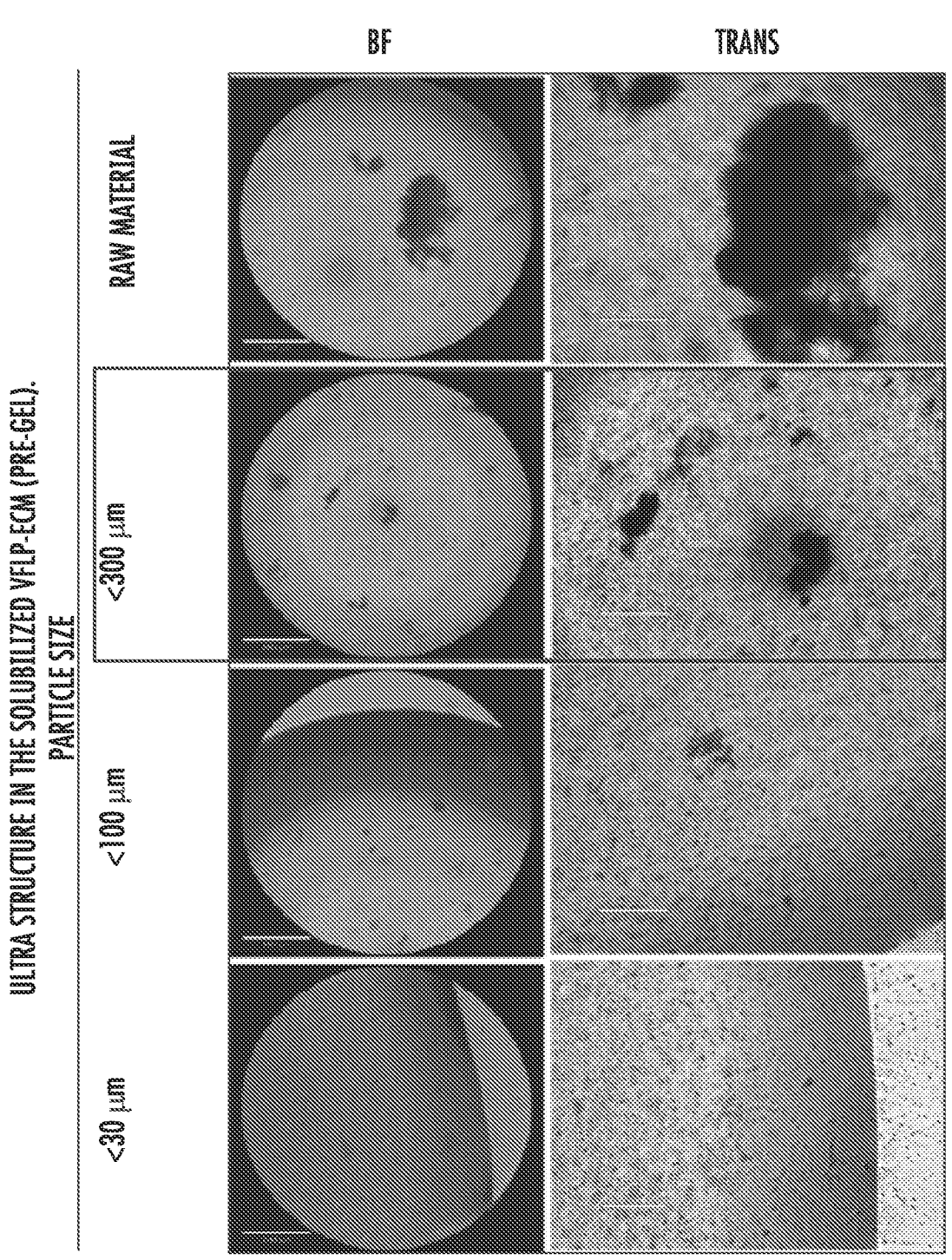
FIGS. 12A and 12B show the results of injectable VFLP-ECM hydrogel characterization.
Figure 12B:
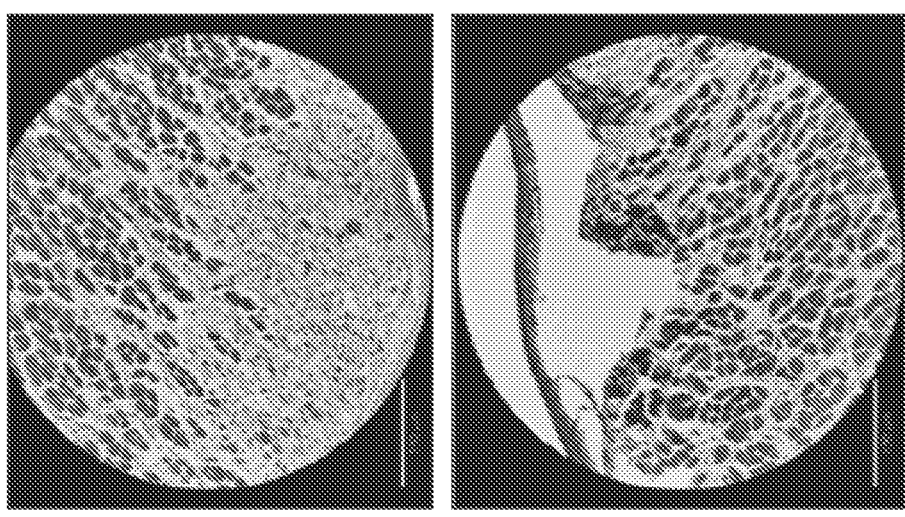
Figure 12B:
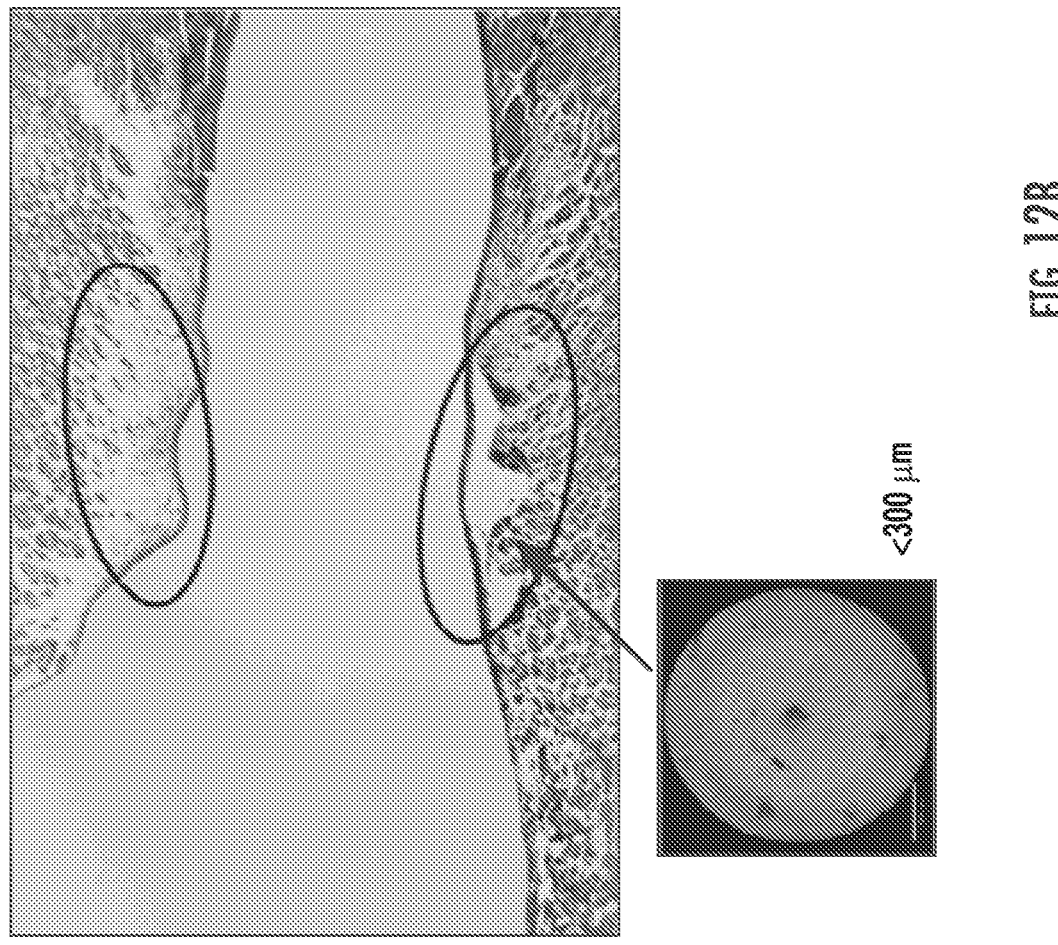

The solubilized ECM-product can be in line produced as injectable and/or inhalable biomaterial according with the filter mesh used within the bioreactor. Data supporting the control of the particle size (<30, <100, <300 um) and injectability of the material is shown in FIGS. 8, 12A and 12B. The particle size of the resulting material is dependent on the mesh filter used.

Example 3

Assessment of Decellularization (sH-ECM vs. mH-ECM)

The method used to decellularize sH-ECM required approximately 9 hours to complete which is 3 times longer compared to the 3-hours using the automated method developed in this study.

The same decellularization reagents as well as washing steps were used in both methods. The decellularization steps include hypotonic or hypertonic conditions via DI water followed by isotonic or hypertonic conditions using DPBS between every stage for both methods. However, in the case of mH-ECM the exposure time was reduced by 1.5 hours for, but not limited to, enzymatic solution (0.02% trypsin), detergents (3% Tween, 4% sodium deoxycholate), and by 30 minutes for acids in alcohol solution (0.1% v/v peracetic acid in a 4% v/v ethanol solution). The semi-batch reactor platform can be adapted to use different reagents in different sequences in case of particular decellularization optimization requirements.

TABLE 2

Steps in the 3-hour automated decellularization of the porcine heart including reagent and exposure time.

| # | Reagent | Time (minutes) |
|---|---------|----------------|
| 1 | DI Water | 5 |
| 2 | 2X DPBS | 5 |
| 3 | 0.02% Trypsin | 30 |
| 4 | DI Water | 5 |
| 5 | 2X DPBS | 5 |
| 6 | 3% Tween-20 | 30 |

TABLE 2-continued

Steps in the 3-hour automated decellularization of the porcine heart including reagent and exposure time.

| # | Reagent | Time (minutes) |
|---|---------|----------------|
| 7 | DI Water | 5 |
| 8 | 2X DPBS | 5 |
| 9 | 4% Sodium Deoxycholate | 30 |
| 10 | DI Water | 5 |
| 11 | 2X DPBS | 5 |
| 12 | 0.1% Peracetic Acid in 4% ethanol sol. | 30 |
| 13 | 1X DPBS | 15 |
| 14 | 1X DPBS | 15 |

Figure 3:
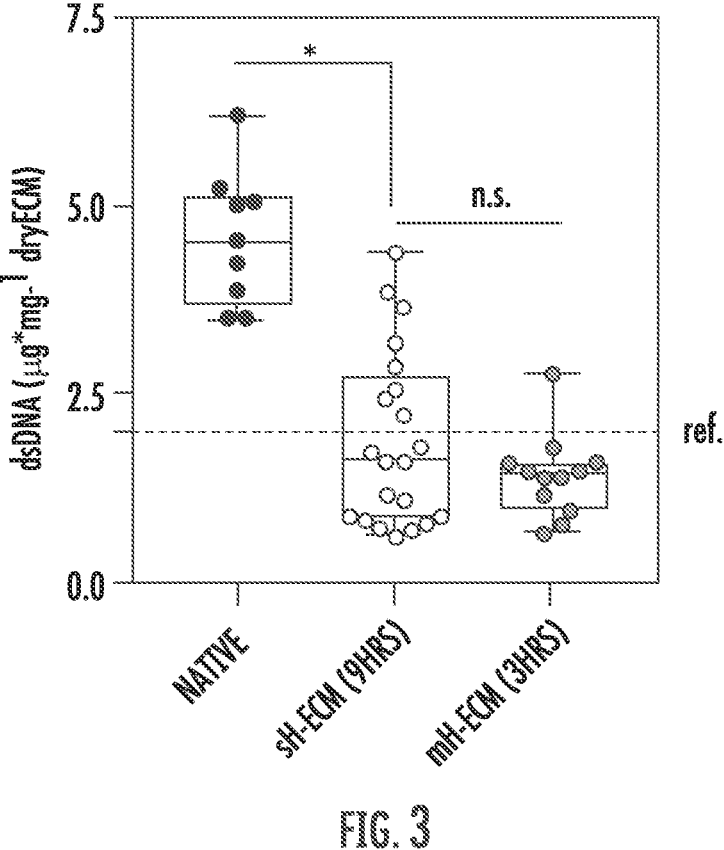
FIG. 3 is a Box and Whisker plot showing double stranded DNA (dsDNA) quantification per mg of dry tissue for native (raw material) and decellularized sH-ECM and mH-ECM. Three independent decellularizations were performed from each heart, so three individual hearts were tested for a total of 9 samples (n=9). The error bars represent the standard error of the means (SEM). *=P<0.05. n.s.=not significant (P>0.05). Reference (ref.) was set at ~2 μg/mg based on Urinary Bladder Matrix (UBM)-ECM reports.

Macroscopic images of the native tissue and the decellularized scaffolds were analyzed and showed a typical transition in color from reddish brown (native tissue) to white (decellularized tissue), which is an indicator of decellularization. Histological analysis was used to evaluate the decellularization quality. The decellularization of both sH-ECM and mH-ECM resulted in a significant reduction in nuclei. The analysis of the H&E staining showed decellularization for both sH-ECM and mH-ECM. The removal of nuclear content was further confirmed via double-stranded DNA (dsDNA) quantification (FIG. 3). The reduction in the amount of dsDNA was consistent with the H&E staining findings. Native tissue yielded a dsDNA content per dry tissue weight of $4.564 \pm 0.299$ µg/mg. A significantly decreased dsDNA content was observed for both sH-ECM ($1.872 \pm 0.253$ µg/mg) and mH-ECM ($1.399 \pm 0.158$ µg/mg). Furthermore, there was no statistically significant difference between sH-ECM and mH-ECM (P>0.05) indicating that the new decellularization method produced a comparable ECM-scaffold. Additionally, the values for sH-ECM and mH-ECM are similar to the dsDNA reported for a commercially available scaffold UBM-ECM used as a commercial reference.[21]

Example 4

Discovery Proteomics Comparing sH-ECM and mH-ECM

Figure 4:
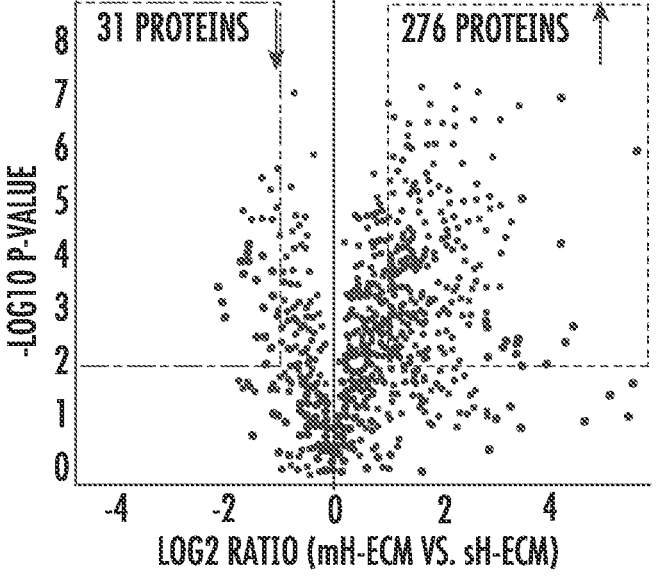
FIG. 4 is a volcano plot representing in the x-axis the Log 2 ratio for the identified proteins according to the label-free quantification (LFQ) analysis and the y-axis the −Log 10 P-value according to the statistical analysis considering a false discovery rate of 0.01. The top left rectangle area (enclosing 31 proteins) corresponds to the statistically significant area for less abundant proteins identified (i.e., Log 2 ratio<1 & P-value<0.01). The top right rectangle area (enclosing 276 proteins) corresponds to the statistically significant area for the identified proteins with higher abundance (i.e., Log 2 ratio>1 & P-value>0.01) in the automated decellularization method for heart compared to the manual method.

To characterize the protein composition and abundance in the decellularized scaffolds, we utilized discovery proteomics strategies to evaluate the main difference in composition between automated mH-ECM and the standard sH-ECM. The data was processed with Proteome Discoverer V 2.4 and the assay identified and associated into master proteins approximately 1000 groups of proteins for both mH-ECM and sH-ECM scaffolds. A Venn diagram showed no major differences in the total number of identified proteins between the two protocols tested. The protocol for sH-ECM yielded a scaffold with seven master proteins not identified in mH-ECM. Meanwhile, mH-ECM presented 14 proteins that were not identified in sH-ECM. The volcano plot shown in FIG. 4 presents the overall changes in protein abundance measured. In general, the plot displays a large number of identified proteins with higher abundance for the mH-ECM condition (positive log 2 fold change ratio), which suggests that the mH-ECM scaffold derived using the automated method preserves a higher abundance of the identified proteins compared to sH-ECM (manual method). This trend is also seen when delimited areas for low or high abundance proteins by selecting proteins within P-values equal or lower than 0.01 (i.e., Log 10 P-values>2) and at least +/−2x ratios (i.e., Log 2 ratio>1). A total of 31 proteins were identified as less abundant in the mH-ECM (upper left), which is significantly lower than the 276 proteins that were identified with a higher abundance in the mH-ECM (upper right).

The significant group of proteins categorized as extracellular matrix proteins was listed out by using cellular component gene ontology analysis. From the list the four lowest and highest Log 2 ratio were plotted. The analysis revealed that structural Collagens type 4, 6, and 3 were less abundant in a range of 2-4 times in the mH-ECM than in the sH-ECM. On the other hand, the analysis also showed that proteoglycans, glycoproteins, and other ECM-proteins with highest abundance were in a range of 4-32 times in the mH-ECM. The data revealed that proteins were more abundant in the mH-ECM than in the sH-ECM. See also Table 3 below.

TABLE 3

| Gene ID | Log2 fold change (LFQ automated_Heart − LFQ manual_Heart) |
| --- | --- |
| COL4A1 | −1.718 |
| COL4A2 | −1.608 |
| COL4A3 | −1.415 |
| COL6A1 | −1.318 |
| COL6A5 | −1.252 |
| COL6A2 | −1.191 |
| COL6A1 | −1.133 |
| VWA1 | 1.049 |
| MFGE8 | 1.052 |
| COL14A1 | 1.055 |
| MGP | 1.103 |
| HSPB6 | 1.108 |
| TF | 1.165 |
| GPX5 | 1.205 |
| BCAM | 1.207 |
| LPL | 1.262 |
| ABI3BP | 1.346 |
| BGN | 1.402 |
| GC | 1.59 |
| B2M | 1.622 |
| ALB | 1.739 |
| DCN | 1.902 |
| COL18A1 | 1.967 |
| ANXA2 | 1.972 |
| AHSG | 2.073 |
| HPX | 2.107 |
| HP | 2.192 |
| PPIA | 2.256 |
| TXN | 2.28 |
| CAPNS1 | 2.869 |
| GPI | 3.396 |
| FMOD | 4.416 |
| NPPA | 5.536 |

Example 5 mH-ECM Optimization (mH-ECM-O) and Cytocompatibility

Although there are no standard parameters for decellularized ECM, Crapo et al.

have proposed the following criteria: <50 ng dsDNA per mg of dry weight ECM, <200 base pairs DNA fragment length, and no visible nuclei in 4',6-diamidino-2-phenylindole (DAPI) and hematoxylin and eosin (H&E) staining. These criteria have been reconsidered since, according to Cramer et al., they may be too limiting, and ECM-scaffolds with dsDNA much greater than 50 ng per mg dry weight tissue have been used without adverse outcomes.[2,21] Despite there being no standardized criteria, dsDNA removal is accepted as an indicator of decellularization level and a good parameter for monitoring the optimization of the process.

The system described in this study can be used as a scalable platform to further optimize the decellularization process for soft tissues from different sources/donors, such as porcine heart and VFLP.

Figure 5A:
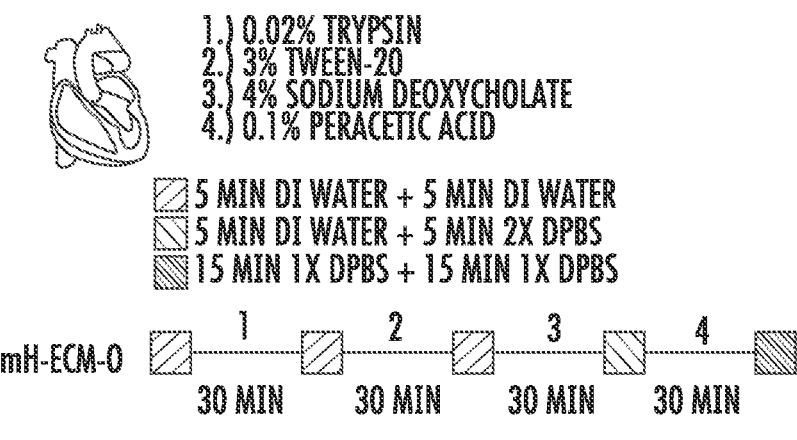
FIGS. 5A-5B illustrate methods for and results of optimized automated heart tissue decellularization.

The decellularization protocol was adjusted by focusing on increasing the dsDNA removal. FIG. 5A shows a schematic of the protocol used to further optimize the dsDNA removal of porcine heart tissue. The fabrication time and decellularization reagents used were the same as those used for the mH-ECM protocol described in Example 3 above.

Figure 5B:
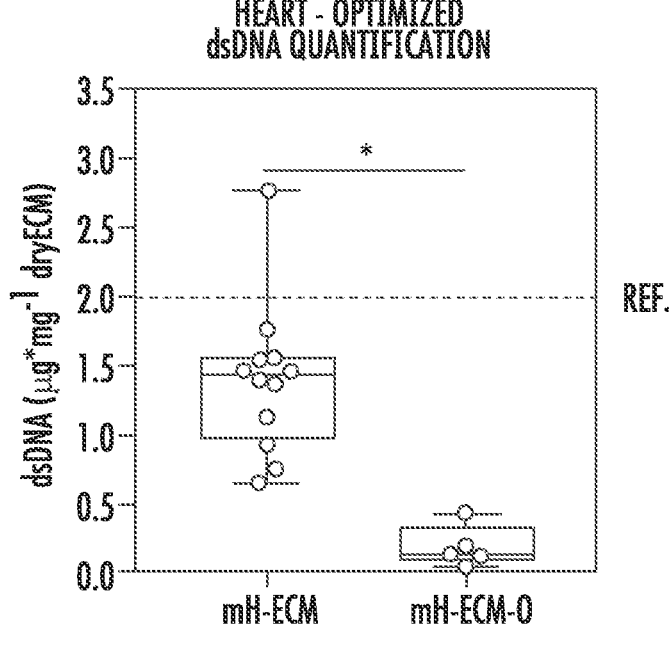

The difference between the protocols in FIG. 5A versus those described in Example 3 lies on the first three wash steps. The 5 minutes DI water followed by 5 minutes 2× DPBS steps were replaced with two consecutive DI water washes of 5 minutes each to facilitate nucleic acid solubility and removal from the ECM-material. Additionally, mechanical stirring was used. The outcome of the adjusted system is presented in FIG. 5B, where the optimized mH-ECM (mH-ECM-O) yielded a DNA content per dry tissue weight of 0.187±0.065 µg/mg which is significantly lower (P<0.05) than mH-ECM.

Figure 6A:
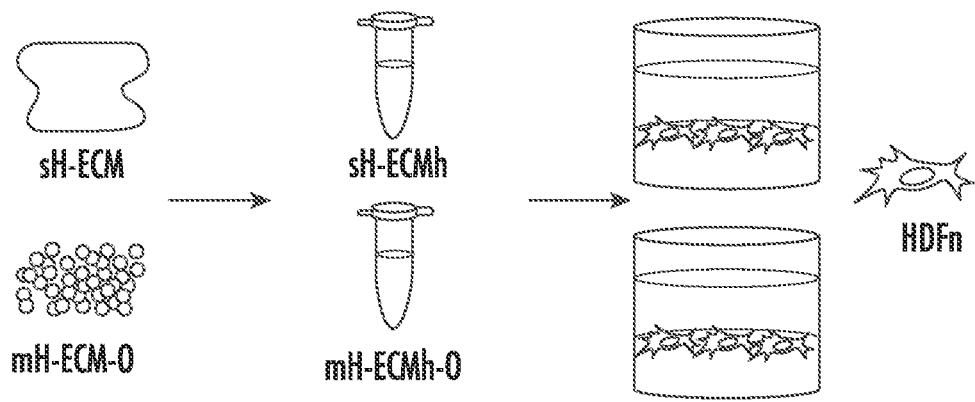
FIGS. 6A and 6B show the results of cytocompatibility studies.
Figure 6B:
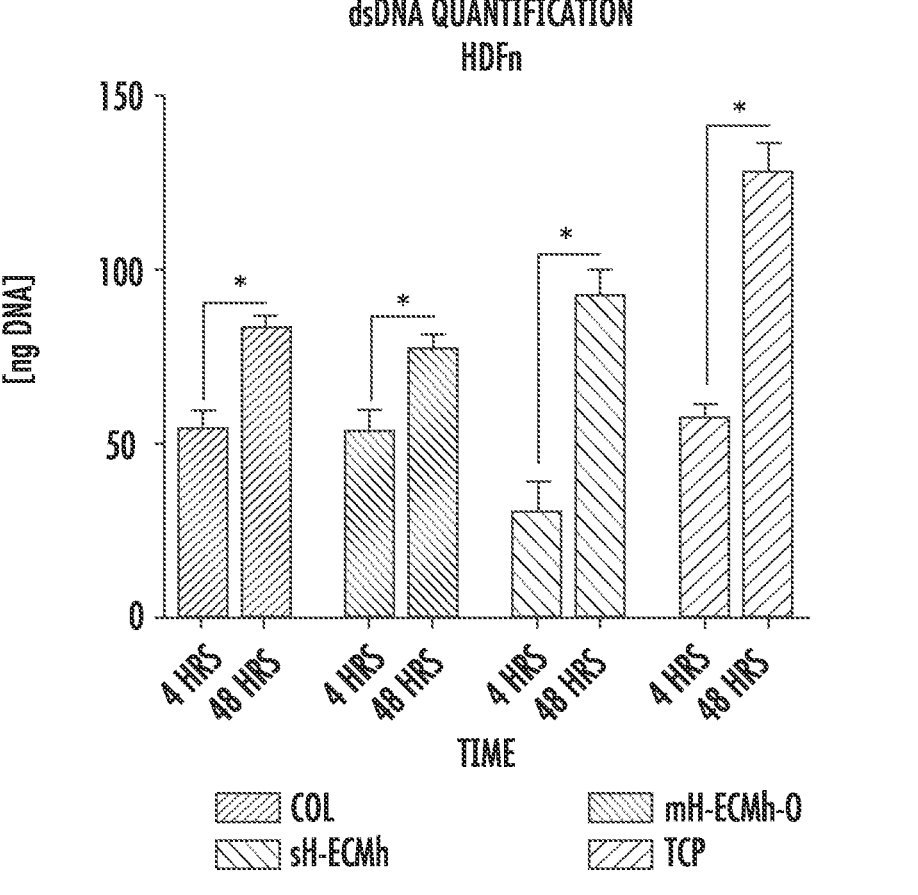

The mH-ECM-O was collected and solubilized into an ECM-hydrogel (mH-ECMh-O) to study its cytocompatibility evaluated via dsDNA quantification on cells cultured on the hydrogel (FIGS. 6A-6B) and by imaging using the LIVE/DEAD Cell Viability assay. The hydrogel without cells was used as a blank/reference to subtract any potential background from the scaffold in the dsDNA measurement. In addition, tissue culture plastic (TCP), Collagen Type I (Col), and sH-ECMh were used as controls. HDFn cells were cultured and the dsDNA was measured after 4 hours of cell attachment and at the end point of the experiment after 48 hours. FIG. 6B depicts values of dsDNA, which reveal a significant (P≤0.05) increase in dsDNA content over time which is consistent across all conditions. The dsDNA measurement was corroborated with LIVE/DEAD imaging (not shown). HDFn cells cultured on TCP, mH-ECMh-O, sH-ECMh, and Col show a Calcein-AM (Green) staining after 24 and 48 hours in culture. Little to no Ethidium Homodimer-1 (Red) staining was detected.

Example 6

Automated Decellularization of VFLP and Cytocompatibility

Vocal fold lamina propria (VFLP), was selected to evaluate the robustness of the decellularization platform. A biological pool of 40 VFLPs was prepared from 20 different animals and the decellularization was performed three independent times (n=3). The decellularization approach used was similar to heart tissue and was aimed towards a reduction in the total time of the decellularization process.

TABLE 4

Steps in the 2.5-hours automated decellularization of porcine VFLP including reagent and exposure time.

| # | Reagent | Time (minutes) |
| --- | --- | --- |
| 1 | DI Water | 5 |
| 2 | 2X DPBS | 5 |
| 3 | 4% Sodium Deoxycholate | 30 |
| 4 | DI Water | 5 |
| 5 | 2X DPBS | 5 |
| 6 | DNAse (273 Kunitz/mL) | 30 |
| 7 | DI Water | 5 |

TABLE 4-continued

Steps in the 2.5-hours automated decellularization of
porcine VFLP including reagent and exposure time.

| # | Reagent | Time (minutes) |
|---|---------|----------------|
| 8 | 2X DPBS | 5 |
| 9 | 0.1% Peracetic Acid in 4% ethanol sol. | 30 |
| 10 | 1X DPBS | 15 |
| 11 | 1X DPBS | 15 |

Figure 7A:
FIGS. 7A-7C show the results of vocal fold lamina propria decellularization.
Figure 7A:
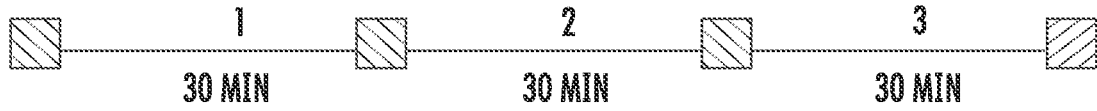

FIG. 7A shows a schematic of the automated method used to decellularize porcine VFLP in approximately 2.5 hours. The automated method was 2.5× faster in comparison with the method used to decellularize porcine VFLP sheets (sVFLP-ECM), which takes approximately 6 hours.[19]

Figure 7B:
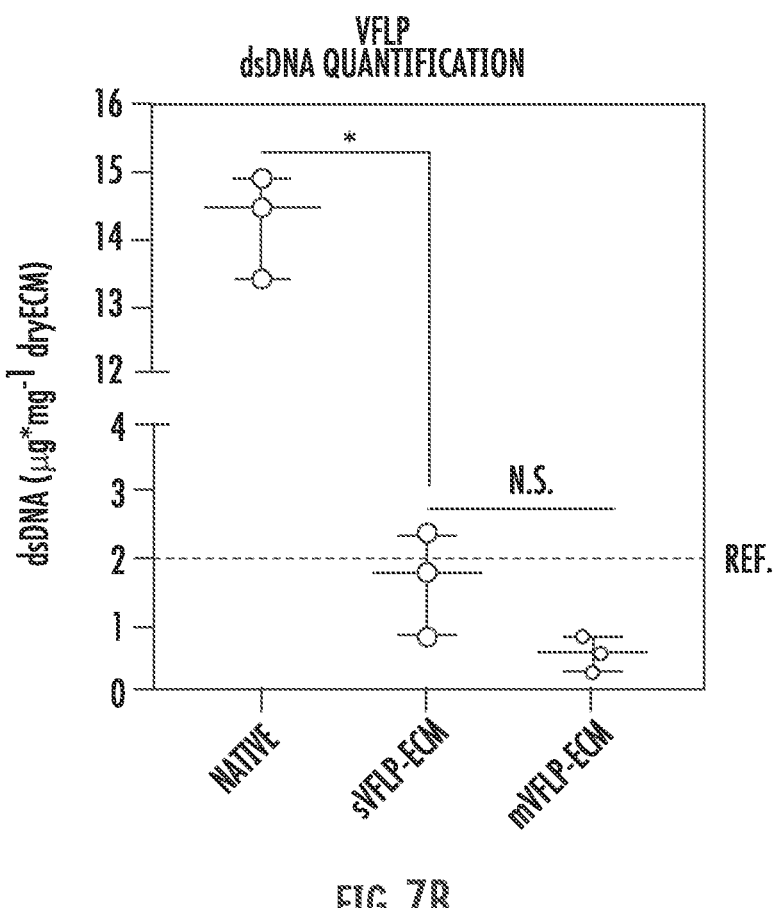

The same decellularization reagents were used for both methods. However, in the case of mVFLP-ECM, the exposure time was reduced by 1.5 hours for 4% sodium deoxycholate and by 1.5 hours for the DNAse treatment. In addition, the first three washes with 1× DPBS for 15 minutes each were replaced with 5 minutes DI water followed by 5 minutes 2× DPBS washes. Same as for mH-ECM, mechanical stirring was used. The dsDNA content (FIG. 7B) for both sVFLP-ECM (1.630±0.439 μg/mg) and mVFLP-ECM (0.535±0.158 μg/mg) was significantly lower (P<0.05) than native VFLP (14.285±0.442 μg/mg). Although the dsDNA content of the mVFLP-ECM was lower and the lot-to-lot variability was minimized, there was no statistically significant difference between sVFLP-ECM and mVFLP-ECM (P>0.05). Both sVFLP-ECM and mVFLP-ECM were similar to the dsDNA reported for the commercially available UBM-ECM.

Figure 7C:
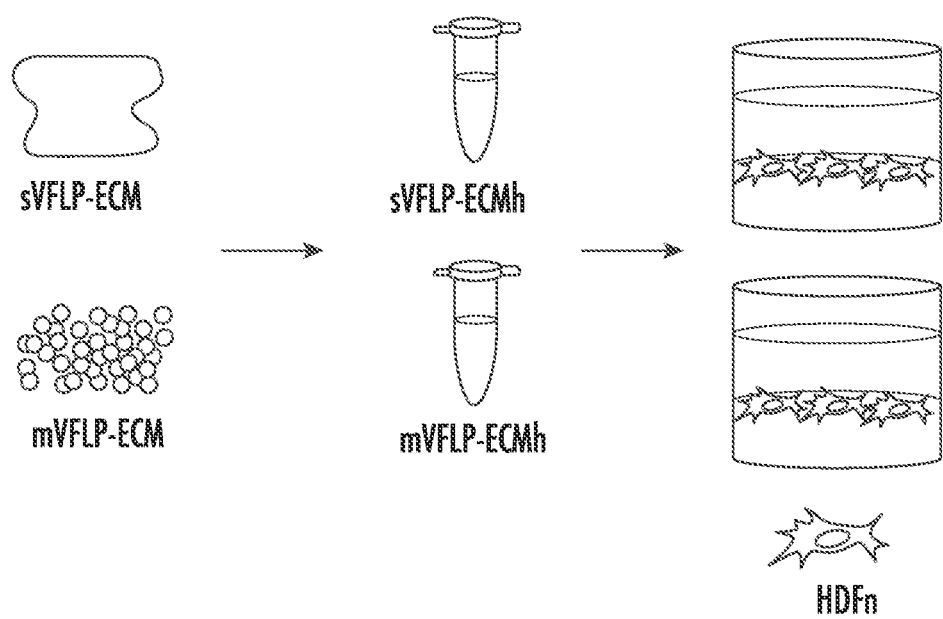

Finally, mVFLP-ECM was solubilized into a hydrogel (mVFLP-ECMh) (FIG. 7C) to study its cytocompatibility by using the LIVE/DEAD Cell Viability assay after culturing HDFn cells. Cell survival after 24 and 48 hours of seeding on top of mVFLP-ECMh and sVFLP-ECMh was imaged and assessed (images not shown).

Discussion of Examples 1-6

Decellularized ECM-based products have been in the market for over 10 years. More and more acellular ECM scaffolds have gathered enough evidence to transition to preclinical trials and most recently an injectable heart ECM hydrogel finished phase I trials and will soon continue to phase II trials.[11] New biofabrication technologies such as 3-D printers that use ECM based bio-inks and injectable therapeutic materials will increase the demand for ECM scaffolds. These applications require a biomaterial fabrication process with controlled lot-to-lot variation and the capacity for customization. Even though the decellularization of various tissues from different sources has been widely explored, the automation and the manufacturing process to standardize the derivation of injectable ECM scaffolds remain poorly studied. Factors such as the inherent variability of tissues and organs, harvesting conditions, methods and reagents used, manual labor, and the labor-intensive (manual labor time>8 continuous hours and often perform by different people) requirements of the current protocols are variables preventing the standardization and optimization of the decellularization process.

In order to achieve decellularization and significantly reduce the production time at each step, our experimental approach (FIG. 1B) involved a closed semi-batch bioreactor and a specific pre-treatment of the native tissue. The baseline method selected for comparison was the production of heart ECM scaffold (sH-ECM—FIG. 1A) derived using a batch decellularization protocol where the user manually switches each of the decellularization reagents in a stepwise process. It is important to note that current decellularization processes involve manual labor (often by multiple users) and require user input at every step of the batch process.[16, 22] The personnel requirement represents a limiting step to reduced production time and can introduce substantial variability in the final product.

A platform aiming at the reduction of a labor-demanding decellularization process of porcine abdominal aortas was presented by Pellegata et al. using an automated and modular device for the decellularization of aortic tissue.[23] Pellegata's method involved approximately 1-2 days of tissue preparation: drying, storing at −80° C., defrosting for 12 hours at −20° C. and overnight at 4° C. After tissue preparation, Pellegata's method took IV cycles of decellularization reagent exposure counting approximately 87 hours in order to produce a successful ECM product comparable to their control (i.e., manual aortic decellularization). In the method described herein, the micronization and the semi-batch bioreactor settings led to significantly shorter decellularization times compared to flat or cylindrical sheets. The size reduction of the native tissue required the adaptation of an appropriate filtration method and proper mechanical stirring of the micronized soft tissue. The automated system described in the present study enabled us to automate the decellularization process for a variety of soft tissues (e.g., heart, VFLP, SG) in a shorter time, facilitating future downstream production of ECM hydrogels and other solubilized forms of the ECM.

Figure 15:
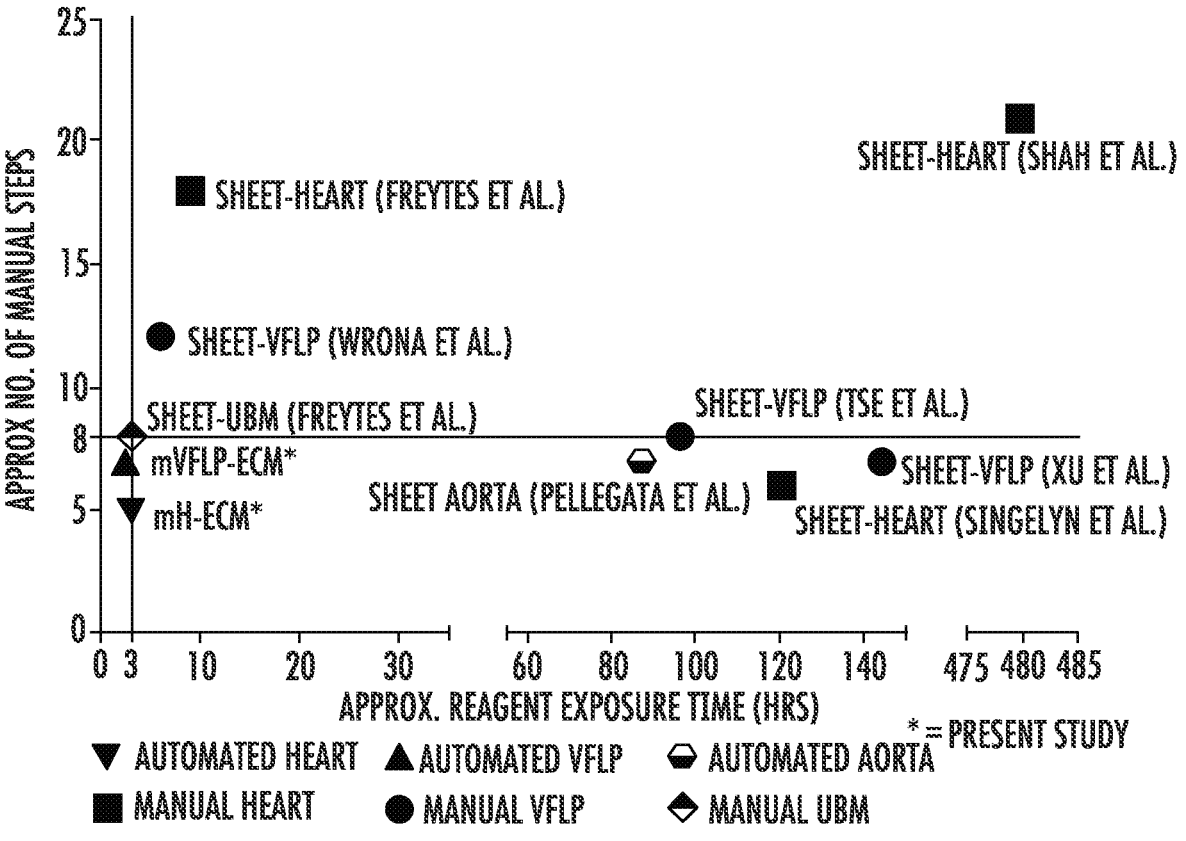
FIG. 15 shows a graph comparing manual and automated decellularization methods. The graph shows the approximate reagent exposure time vs. approximate number of manual steps for the automated method (mH-ECM and automated VFLP-ECM) and currently available methods for the decellularization of heart, aorta, VFLP, and UBM. The approximate reagent exposure time was calculated without taking into account tissue processing steps. Overnight steps were assumed to equal 8 hours.

The efficiency in the heart decellularization was compared against the sH-ECM (reference protocol selected) that if run continuously should take approximately 9 hours to complete.[18] It is important to notice that the selected protocol is shorter than some of the other protocols available for heart tissues that may require 48-72 hours or even weeks depending on the decellularization reagents used (FIG. 15). As an example, the method used by Singelyn et al. to produce decellularized myocardial matrix and being used in clinical trials, may take approximately 96-144 hours.[11, 24] Another example is the method by Shah et al. which takes approximately 2.5 weeks to obtain thin slices of decellularized porcine myocardium.[25] The data suggest that the 3 hours automated semi-batch process presented an efficiency similar to the 9 hours method using the same sequence of decellularization reagents. The similarity in the decellularization sequence between both methods (3 and 9 hours) allows a better comparison regarding cytocompatibility effects elicited by the scaffold's materials. Indeed, the significant number of lab-specific decellularization protocols, as well as the lot-to-lot variation, represent a challenge for studying tissue specificity and limit the reproducibility of the findings. Typically, each laboratory group selects or develops their own decellularization protocol that varies depending on the particular tissue of interest, site-specific limitations, and scientific approaches used by the lab.[26] For example, as shown in FIG. 15, there are at least 3 different protocols to decellularize heart sheets. Even though the ECM derived from these studies had encouraging biological responses, it remains a challenge to compare them due to the different decellularization methods used and our inability to distinguish if the effect is as result of the final product or the ECM itself. Nevertheless, FIG. 15 highlights the significant improvements on both time and steps needed to decellularize two soft tissues when using the automated system described in this study. The presently disclosed systems and methods may allow for the development of a "universal" decellularization method that can be applied to any tissue or organ in order to remove the decellularization protocol as a variable during any biological comparison.

The method described in this study involves automated dosing pumps that were connected to an inline filtration bioreactor, allowing for the production of ECM scaffolds. Pre-processing the native tissue via micronization allowed us to significantly reduce the decellularization time as shown in FIGS. 1 and 15. When using the same 3-hour protocol to decellularize heart sheets, the dsDNA removal was above acceptable levels when compared to sH-ECM or the values for UBM-ECM. The data shows high variability in the standard method and all the measured values were higher than the references selected (sH-ECM and UBM-ECM). The size reduction increases the available surface area and facilitates diffusion between the tissue and the reagents. By reducing the decellularization time, this method can significantly reduce production costs. Additionally, due to the reduction in exposure time to decellularization reagents, the ECM ultrastructure and the native protein composition may be better preserved compared to other methods.

We compared the effects of starting the decellularization using a dry (D) native tissue and its effect on variability and dsDNA removal. DNA quantification showed high variability and insufficient DNA removal for sH-ECM (9 hrs D), sH-ECM (3 hrs D), and mH-ECM (3 hrs D). These results were supported by histological examination via H&E which showed intact nuclei after decellularization for freeze-dried tissues (not shown). Therefore, the hydration of the initial micronized material could play a role in the overall efficiency and variability of the process. Future studies will address the use of lyophilized raw material by exploring a re-hydration of the dried tissue particles prior to starting the decellularization given its potential to help with raw material storage and handling during the scale up process. Re-hydration of the tissue prior to starting the decellularization is also explored.

The semi-batch geometry was designed to facilitate waste removal reducing potential interactions between the released dsDNA and the acellular ECM scaffold. Even though the semi-batch system was designed as a closed environment to maintain sterility of the product during the decellularization process, further studies address additional pre-treatments such as bioburden reduction. However, Hernandez et al. tested this variable on ECM decellularization and concluded that there was no major effect on the ECM scaffolds.[9] The process described in this study opens up the possibility to monitor pertinent parameters in real time (on line and in line) during the decellularization process to ensure optimal ECM scaffold production.

In order to evaluate if the semi-batch method affects global protein content, we performed discovery proteomic analysis comparing the manual heart protocol (reference) with the automated heart protocol. The data showed that the overall number of proteins present after decellularization between the automated (3 hrs) method and the standard protocol (9 hrs) was not affected. However, the relative abundance of a few structural collagens (type 3, 4, 5, and 6) was significantly reduced in the automated method. This could be explained by the increase in surface area and the potential elution of these proteins from the final product during waste removal. However, not all collagens were significantly reduced. Collagens 1 and 2 were identified in a similar abundance in the ECM obtained with the automated method. Collagen 1 and 2 are of interest due to their association with fibrosis studies.[27] In general, a larger number of ECM related proteins remained in the scaffold obtained with the automated method. Natriuretic peptides precursor A and Fibromodulin (NPPA, FMOD) were among the most abundant proteins identified in the 3 hours acellular ECM (about 30x higher compared to the 9 hours protocol). NPPA belongs to the family of Natriuretic peptides whose role have been associated with cardiovascular physiology and host metabolism.[28] Also, previous studies have reported the potential benefits of increasing the concentration of these type of peptides in patients.[29-30] FMOD is a proteoglycan that has been reported as an important ECM protein involved in angiogenesis, the regulation of scar formation in skin, and in cardiac remodeling. Another abundant proteoglycan in the scaffold obtained with the automated method was Decorin (DCN), which has been associated with regulating extracellular matrix integrity, angiogenesis, and fibrosis. Previous studies suggest DCN interacts with various growth factors such as transforming growth factor beta (TGFβ). An in vitro study with human cardiac fibroblasts showed that DCN downregulated collagen production following TGFβ stimulation.[39] The abundance of these proteins in the ECM warrants further investigation to determine their effect in vitro and in vivo.[31-33] The automated platform presented in this study proposes an efficient tool for screening multiple protocols aiming at the retention or removal of particular proteins.

Further optimization can be achieved with the semi-batch system by focusing on dsDNA removal and the retention of a particular ECM component (e.g., retention of collagens) via the evaluation and selection of specific decellularization reagents. Although some commercial acellular ECMs may contain a higher amount of dsDNA, a recent report stated that this does not limit their clinical applications.[2] Furthermore, the mH-ECM scaffold and the mH-ECM-O described in this study had lower dsDNA concentration than the UBM-ECM.[21] Therefore, the platform was used to optimize the mH-ECM by improving the mechanical stirring of the tissue and by adding a 5-minute wash/rinse using DI water immediately after exposure to reagents. The data shows that this condition was able to increase the removal of the dsDNA with a final ECM scaffold with dsDNA values in the nanogram range per mg of dry tissue. In addition to dsDNA removal, future studies will target other parameters such as preservation of specific ECM proteins, reduce variability, and in-line monitoring of the decellularization process. The semi-batch system developed is a versatile platform that produces ECM scaffolds ready for transformation into hydrogel forms in an efficient manner. In addition, the platform can be used for the in situ production of other solubilized scaffolds or biomaterials such as Matrix-Bound vesicles (MBVs) production using downstream solubilization methods.[21, 34-36]

To show the adaptability of the automated system, the semi-batch bioreactor system was tested using vocal fold lamina propria. The VFLP protocol selected for comparison took approximately 6 hours to complete in a labor dependent manner using sodium deoxycholate, DNAse I, and peracetic acid.[19] Another available protocol for the decellularization of VFs involves a 4-day treatment with SDS.[37] SDS treatment for an extended period of time is known to be cytotoxic if not properly removed, disrupt the ECM ultrastructure, remove GAGs and growth factors, and damage collagens.[15] As the VFLP is rich in ECM proteins, the method used does not include either trypsin or Tween in order to increase ECM preservation. To achieve a reduction in the reagent exposure times, the tissue was frozen and grounded, and the pumps were set to run a 2-3 hour protocol following the timeline presented in FIG. 7A. The dsDNA removal met the target of less than 2 μg/mg of dry tissue. When comparing collagens retention, the automated method performed significantly better by retaining a higher abundance of collagen proteins detected via proteomic discovery than the sheet or classical method as shown in Table 1 and FIG. 13. These results show the versatility of this new system and its potential use with a variety of tissues (e.g., soft tissues).

ECM scaffolds can be used for various clinical applications in sheet form which are typically sutured into the wound, and a hydrogel form can be easily injected into the site of injury using minimally invasive methods. Therefore, the cytocompatibility of heart ECM hydrogels derived with this automated method was tested using HDFn. The hydrogel was produced outside of the bioreactor using a previously described method by Freytes et al.[13] The viability of HDFns was determined via dsDNA quantification at 24 and 48 hours of culture. HDFns grew and proliferated in the micronized ECM hydrogels as shown in FIGS. 6A and 6B. The LIVE/DEAD (green/red) staining confirmed these results and showed the cells alive and with an elongated morphology typically associated with healthy fibroblasts.[38] The green stain was heavily represented throughout the samples and the red stain was barely detected suggesting a high survival rate over 24 and 48 hours (images not shown). Similar results were obtained for HDFns cultured on VFLP-ECM hydrogels derived with the automated system (images not shown). To investigate self-assembly, we measured gelation kinetics of ECM hydrogels derived from each method.

After hydrogel preparation, 100 μL of hydrogel/well at least in triplicate were aliquoted in a 96-well plate and kept on ice until measurement. The samples were measured using a BioTek SYNERGYneo2 multimode reader pre-heated to 37° C. Absorbance measurements were taken at 405 nm every 1 minute for 90 minutes. The data was normalized using the following equation:

$$\text{Normalized absorbance}_{405\ nm} = \frac{(A_x - A_{min})}{(A_{max} - A_{min})}$$

Where Ax=experimental measurement, Amin=minimum absorbance, Amax=maximum absorbance. The data was graphed using Prism 8.0.

Our data shows that sH-ECMh, mH-ECMh, sVFLP-ECMh, mVFLP-ECMh hydrogels exhibited sigmoidal curves similar to collagen type I confirming hydrogel formation. These results show that the automated system described in this study can produce high quality ECM hydrogel from multiple soft tissues.

The disclosed approach is applicable for other tissues (e.g., skeletal muscle, dermis, lung etc.) and can lead to a standard "universal" decellularization method applicable to any tissue. Additionally, the present disclosure will be applicable for the production of downstream acellular ECM biomaterials (e.g., hydrogels, solubilized, and MBVs) inside the bioreactor to maintain sterility and the automated scale-up of the decellularization process. While the disclosed decellularization protocol is performed in 50 mL bioreactors, the same can be applied to industrial scale bioreactor systems (0.5 to 5 L) that will allow for increased ECM yields and higher production rates. By incorporating in-line monitoring of the process, the automated system can in some embodiments self-adjust to provide an attractive platform for rapid tissue decellularization.

The combination of pre-treating of soft tissues via size reduction, bioreactor design, inline filtration, the addition of hypotonic or hypertonic short washes, and mechanical dissociation of the tissue via continuous stirring enabled us to develop an automated semi-batch bioreactor system for the production of ECM hydrogels. The system significantly reduced the production time and consistency of ECM scaffolds from soft tissues (heart and vocal fold lamina propria) while preserving ECM content and maintaining cytocompatibility.

Example 7

Derivation of Injectable-ECM Inside the Bioreactor

FIG. 8 depicts four filtration-bioreactor settings (a, b, c, and c+) to produce injectable-ECM with a particle size distribution according with the filter used and appropriate with the needle specifications associated with the application: (a) 80 mesh (opening=178 microns); (b) 50 mesh (opening=304 microns), and (c) and (c+) 20 mesh (opening=915 microns). In FIG. 8, the internal liquid level is delimited with the brackets. While FIG. 12A shows bright-field microscopy images of injectable VFLP-ECM fractions with ECM particle in suspension but in a defined particle size according with the filter used. We have enclosed in a rectangle frame the optimal injectable particle size (<300 μm) to be used in a vocal fold animal model via 25-gauge needle. FIG. 12B depicts the histological section of the animal model used (rabbit vocal folds) showing the VFLP-ECMh injection site (black arrow, 4× magnification). FIG. 12B insert shows the injection site at 10× magnification, enabling the visualization of the void that resulted in the lamina propria after injection of VFLP-ECMh. These histological images evidence that the development of an appropriate manufacturing method for the derivation of injectable solubilized ECM within bioreactor.

Example 8

ECM Aerosolization Methods

A diluted ECM solution (125 μg/mL) was prepared from the stock ECM solution (10 mg/mL) using Milli-Q water acidified with 0.1 M HCl. Then the ECM solution was neutralized to a pH of 7.3+/−0.2 using 0.1 M NaOH. Next, the diluted ECM solution was transferred gradually (3 mL at a time) into a 50 μm filter placed in a 50 mL conical tube. The tube with the solution and filter was centrifuged for 5 minutes at 1000 RPM. The filtration process was repeated until the entirety of the solution was filtered. The final solution was aerosolized using a nebulizer (e.g., mesh or jet nebulizers).

Figure 14A:
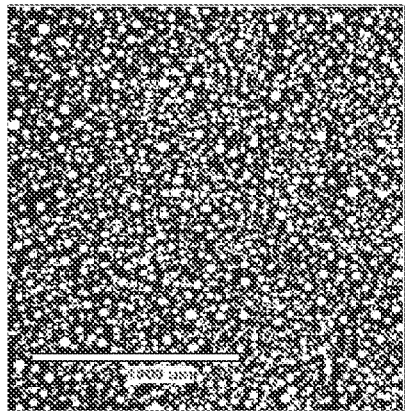
FIGS. 14A, 14B and 14C show the results of ECM nebulization.
Figure 14B:
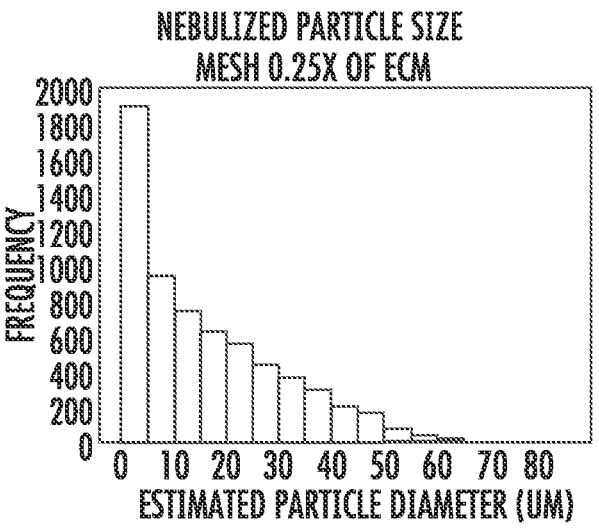
Figure 14C:
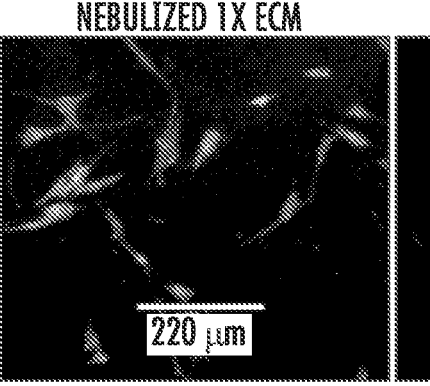
Figure 14C:
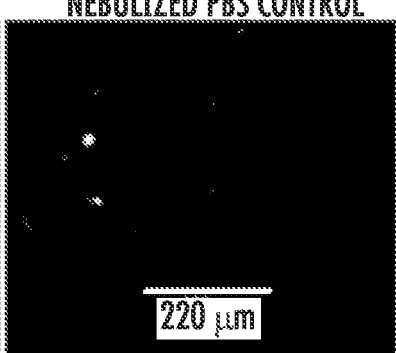

The results of ECM nebulization are shown in FIGS. 14A, 14B and 14C. FIG. 14A shows a microscopic view of ECM nebulized collected on a non-tissue culture treated surface. Particle size analysis distribution for nebulized ECM collected on a non-tissue culture treated surface is shown in FIG. 14B. The lower range of particles (size<15 μm) obtained evidence of the material's feasibility to reach both upper and lower respiratory targets. Finally, the results of cell attachment tests (the visible cells are in indication of cell attachment on the surface) are shown in FIG. 14C.

Example 9

In-Line Monitoring via Abs. 260

Figure 10:
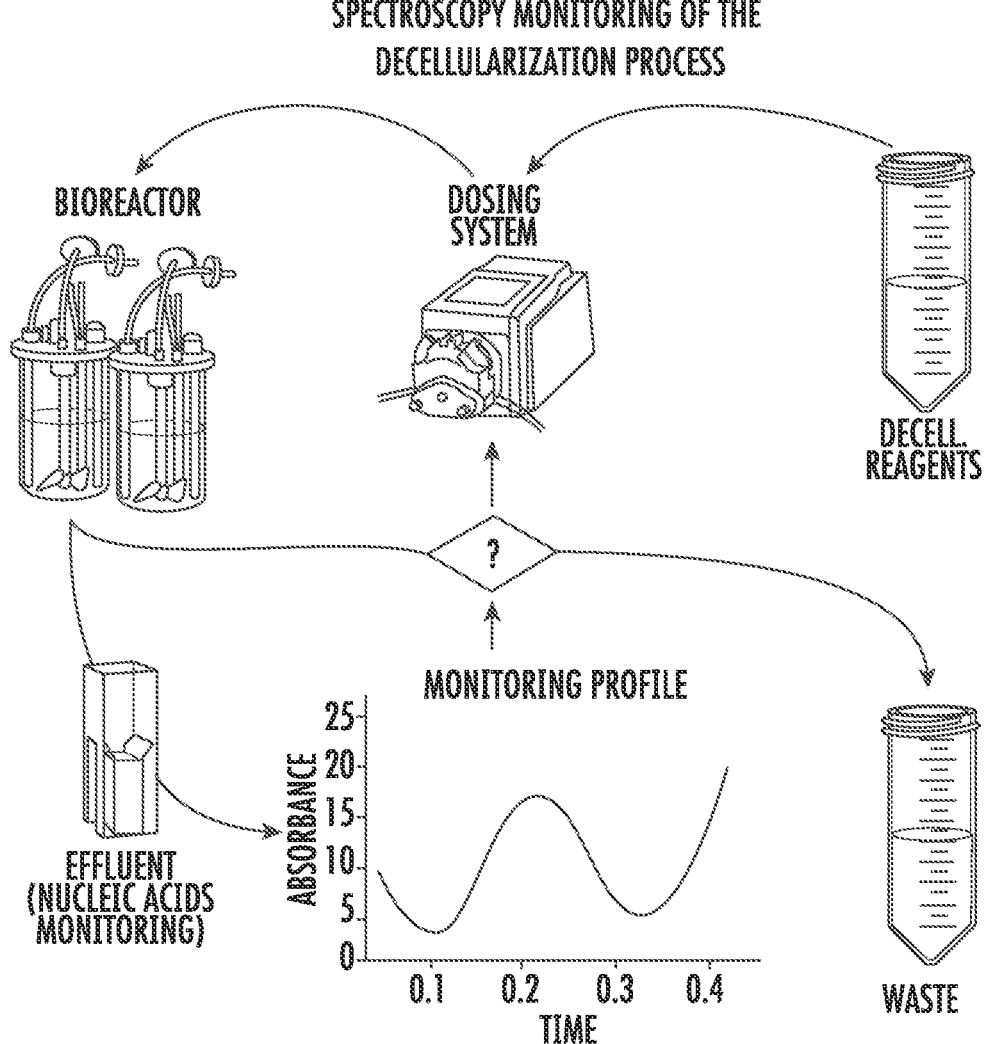
FIG. 10 is a schematic illustration of an in-line or remote monitoring system evaluating the absorbance at 260 nm (Abs. 260 nm) from the bioreactor's effluent (or waste after each decellularization reagent) as a function of the exposure time.

Referring to FIG. 10, a representative approach for in-line monitoring of a decellularization process in accordance with the presently disclosed subject matter. FIG. 10 schematically shows evaluating the absorbance at 260 nm (Abs. 260 nm) from the bioreactors' effluent (or waste after each decellularization reagent) as a function of the reagent exposure time. Aliquots from the bioreactor are taken during the decellularization process for either the classic batch method (sheet, sh) or the semi-batch (automated, au) method. Nucleic acids (e.g., DNA) removal dynamics are assessed by plotting the absorbance from the samples at different times tracing the tissue's nucleic acid removal. In some embodiments, the system is adapted to in-line measurement to avoid manually taking aliquots and to make readings in line.

Example 10

Monitoring Profile Using a Semi-Batch Decellularization Approach (au)

Figure 11A:
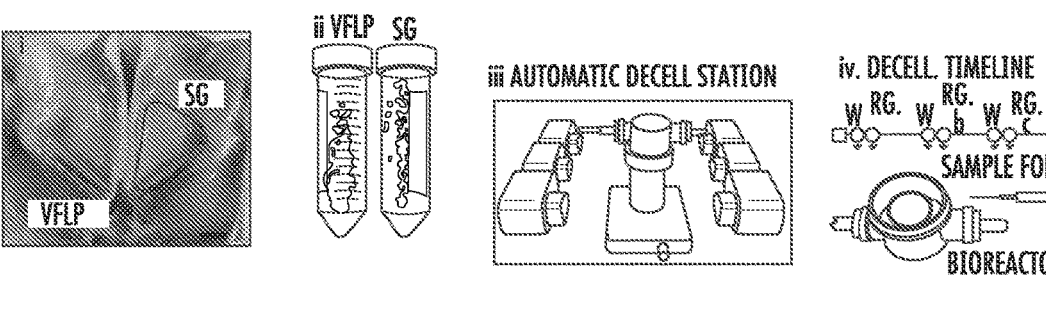
FIG. 11A includes (i) images from an automated decellularized system applied to VFLP and supraglottic (SG) tissue; (ii) chopped particles from pooled VFLPs and SGs: (iii) automated decellularization station setting; and (iv) the effluent sample port for in-line monitoring.

The au-decellularization process uses ground tissue (particle size<3 mm) as a raw native material fed into the bioreactor, as shown in FIG. 11A(ii). The bioreactor has an inline vertical filter and a fluidic system managed via automated dosing pumps FIG. 11A(iii). Once the material is loaded into the bioreactor, the dosing pumps run the protocol for adding or removing the decellularization reagents according to the exposure time programmed; meanwhile, magnetic stirrer bars homogenize the solution. Aliquots representing the bioreactor's effluent status were taken from the container using an inline collection method, as shown in FIG. 11A(iv). The Abs. 260 nm from the aliquoted samples were measured and then plotted as a function of the reagent exposure time to obtain the spectroscopy curves associated with the decellularization.

Figure 11B:
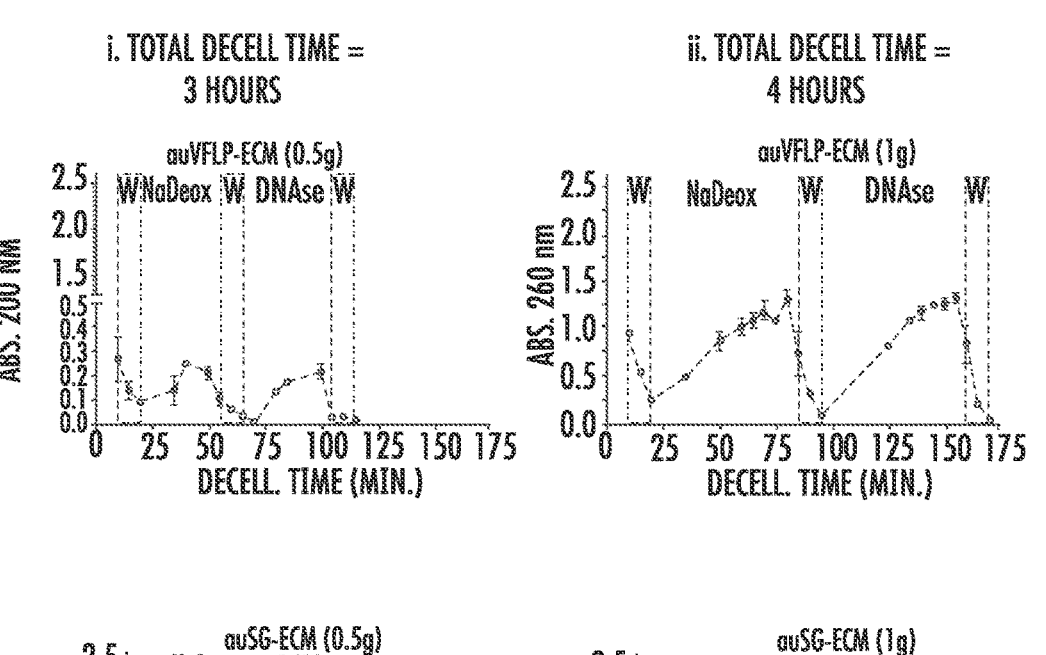
FIG. 11B includes graphs of decellularization monitoring profiles for 0.5 g (i) and 1 g (ii) for each of automated VFLP and automated SG during each decellularization treatment (W=washes, NaDeox=sodium deoxycholate, DNAse=DeoxyriboNuclease A). The error bars represent at least three independent times (n=3).
Figure 11B:
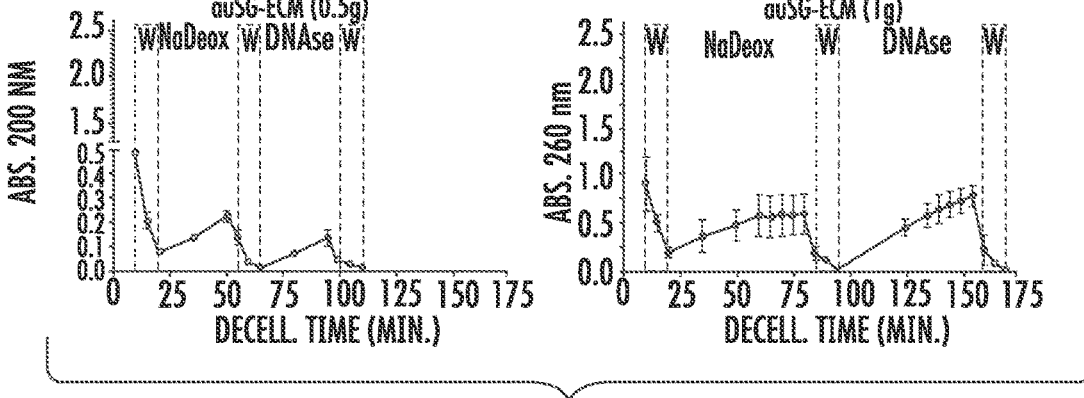

The decellularization parameters were as follow: 1) 3 hours decellularization and 0.5 g of fed native tissue and ii) 4 hours decellularization and 1 g of loaded native tissue; the resulting curves are shown in FIGS. 11B(i) and 11B(ii). Within the W areas, the absorbance showed a reduction trend regarding each wash. For the NaDeox a linear trend was observed within the first 30 min of exposure for both auVFLP and auSG. For auVFLP, the curve for the DNAse treatment showed a plateau like-trend between 80 to 90 min, different to the DNAse profile for auSG for FIG. 11B(i).

FIG. 11B(ii) shows the effect of doubling the load of initial tissue quantity and extending the exposure time from 30 min to 60 min for both NaDeox and. DNAse in the profile curves. For the auVFLP decellularization, the curves showed a similar level of intensity for both NaDeox and DNAse treatments. The NaDeox area profile shows a linear increment trend with an earlier indication of a plateau trend between 60 and 75 min. However, in the case of DNAse and after the point at 130 min, the curve indicates a well-defined plateau trend, which suggests that the system reached a potential endpoint for the treatment. The auSG decellularization profile revealed a clear plateau area for the NaDeox stage, but a not well define plateau was obtained for the DNAse treatment; instead, the DNAse curve for auSG trend suggested a decay in the absorbance after the 130 min time-point. Analogous to the classical sh-method, the intensity of the Abs. 260 nm signal was higher for auVFLP than auSG.

REFERENCES

All references listed herein including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

1. Zhu, M.; Li, W.; Dong, X.; Yuan, X.; Midgley, A. C.; Chang, H.; Wang, Y.; Wang, H.; Wang, K.; Ma, P. X.; Wang, H.; Kong, D., In vivo engineered extracellular matrix scaffolds with instructive niches for oriented tissue regeneration. *Nat Commun* 2019, 10 (1), 4620. DOI: 10.1038/s41467-019-12545-3.
2. Cramer, M. C.; Badylak, S. F., Extracellular Matrix-Based Biomaterials and Their Influence Upon Cell Behavior. *Ann Biomed Eng* 2019. DOI: 10.1007/s10439-019-02408-9.
3. Wade, R. J.; Burdick, J. A., Engineering ECM signals into biomaterials. *Mater Today* 2012, 15 (10), 454-459. DOI: Doi 10.1016/S1369-7021(12)70197-9.
4. Crapo, P. M.; Gilbert, T. W.; Badylak, S. F., An overview of tissue and whole organ decellularization processes. *Biomaterials* 2011, 32 (12), 3233-3243. DOI: 10.1016/j.biomaterials.2011.01.057.
5. Brown, B. N.; Badylak, S. F., Extracellular matrix as an inductive scaffold for functional tissue reconstruction. *Transl Res* 2014, 163 (4), 268-285. DOI: 10.1016/j.trsl.2013.11.003.
6. Jimenez-Gastelum, G. R.; Aguilar-Medina, E. M.; Soto-Sainz, E.; Ramos-Payan, R.; Silva-Benitez, E. L., Antimicrobial Properties of Extracellular Matrix Scaffolds for Tissue Engineering. *Biomed Res Int* 2019, 2019, 9641456. DOI: 10.1155/2019/9641456.
7. Sackett, S. D.; Tremmel, D. M.; Ma, F.; Feeney, A. K.; Maguire, R. M.; Brown, M. E.; Zhou, Y.; Li, X.; O'Brien, C.; Li, L.; Burlingham, W. J.; Odorico, J. S., Extracellular matrix scaffold and hydrogel derived from decellularized and delipidized human pancreas. *Sci Rep* 2018, 8 (1), 10452. DOI: 10.1038/s41598-018-28857-1.
8. Choudhury, D.; Tun, H. W.; Wang, T. Y.; Naing, M. W., Organ-Derived Decellularized Extracellular Matrix: A Game Changer for Bioink Manufacturing? *Trends Biotechnol* 2018, 36 (8), 787-805. DOI: 10.1016/j.tibtech.2018.03.003.
9. Hernandez, M. J.; Yakutis, G. E.; Zelus, E. I.; Hill, R. C.; Dzieciatkowska, M.; Hansen, K. C.; Christman, K. L., Manufacturing considerations for producing and assessing decellularized extracellular matrix hydrogels. *Methods* 2019. DOI: 10.1016/j.ymeth.2019.09.015.
10. Badylak, S. F.; Freytes, D. O.; Gilbert, T. W., Extracellular matrix as a biological scaffold material: Structure and function. *Acta Biomater* 2009, 5 (1), 1-13. DOI: 10.1016/j.actbio.2008.09.013.
11. Traverse, J. H.; Henry, T. D.; Dib, N.; Patel, A. N.; Pepine, C.; Schaer, G. L.; DeQuach, J. A.; Kinsey, A. M.; Chamberlin, P.; Christman, K. L., First-in-Man Study of a Cardiac Extracellular Matrix Hydrogel in Early and Late Myocardial Infarction Patients. *JACC: Basic to Translational Science* 2019, 357. DOI: 10.1016/j.jacbts.2019.07.012.

12. Spang, M. T.; Christman, K. L., Extracellular matrix hydrogel therapies: In vivo applications and development. *Acta Biomater* 2018, 68, 1-14. DOI: 10.1016/j.actbio.2017.12.019.

13. Saldin, L. T.; Cramer, M. C.; Velankar, S. S.; White, L. J.; Badylak, S. F., Extracellular matrix hydrogels from decellularized tissues: Structure and function. *Acta Biomater* 2017, 49, 1-15. DOI: 10.1016/j.actbio.2016.11.068.

14. Efraim, Y.; Schoen, B.; Zahran, S.; Davidov, T.; Vasilyev, G.; Baruch, L.; Zussman, E.; Machluf, M., 3D Structure and Processing Methods Direct the Biological Attributes of ECM-Based Cardiac Scaffolds. *Sci Rep-Uk* 2019, 9. DOI: ARTN 5578 10.1038/s41598-019-41831-9.

15. Fernandez-Perez, J.; Ahearne, M., Author Correction: The impact of decellularization methods on extracellular matrix derived hydrogels. *Sci Rep* 2019, 9 (1), 19818. DOI: 10.1038/s41598-019-56283-4.

16. Simsa, R.; Padma, A. M.; Heher, P.; Hellstrom, M.; Teuschl, A.; Jenndahl, L.; Bergh, N.; Fogelstrand, P., Systematic in vitro comparison of decellularization protocols for blood vessels. *Plos One* 2018, 13 (12). DOI: ARTN e0209269 10.1371/journal.pone.0209269.

17. Dzobo, K.; Motaung, K.; Adesida, A., Recent Trends in Decellularized Extracellular Matrix Bioinks for 3D Printing: An Updated Review. *Int J Mot Sci* 2019, 20 (18). DOI: 10.3390/ijms20184628.

18. Freytes, D. O.; O'Neill, J. D.; Duan-Arnold, Y.; Wrona, E. A.; Vunjak-Novakovic, G., Natural Cardiac Extracellular Matrix Hydrogels for Cultivation of Human Stem Cell-Derived Cardiomyocytes. Radisic, M.; Black Iii, L. D., Eds. Springer New York: New York, N.Y., 2014; Vol. 1181, pp 69-81. DOI: 10.1007/978-1-4939-1047-2_7.

19. Wrona, E. A.; Peng, R.; Born, H.; Amin, M. R.; Branski, R. C.; Freytes, D. O., Derivation and characterization of porcine vocal fold extracellular matrix scaffold. *Laryngoscope* 2016, 126 (4), 928-35. DOI: 10.1002/lary.25640.

20. Wisniewski, J. R.; Zougman, A.; Nagaraj, N.; Mann, M., Universal sample preparation method for proteome analysis. *Nature Methods* 2009, 6 (5), 359-U60. DOI: 10.1038Nmeth.1322.

21. Huleihel, L.; Hussey, G. S.; Naranjo, J. D.; Zhang, L.; Dziki, J. L.; Turner, N. J.; Stolz, D. B.; Badylak, S. F., Matrix-bound nanovesicles within ECM bioscaffolds. *Sci Adv* 2016, 2 (6). DOI: UNSP e1600502 10.1126/sciadv.1600502.

22. Kusuma, G. D.; Yang, M. C.; Brennecke, S. P.; O'Connor, A. J.; Kalionis, B.; Heath, D. E., Transferable Matrixes Produced from Decellularized Extracellular Matrix Promote Proliferation and Osteogenic Differentiation of Mesenchymal Stem Cells and Facilitate Scale-Up. *Acs Biomater Sci Eng* 2018, 4 (5), 1760-1769. DOI: 10.1021/acsbiomaterials.7b00747.

23. Pellegata, A. F.; Asnaghi, M. A.; Zonta, S.; Zerbini, G.; Mantero, S., A novel device for the automatic decellularization of biological tissues. *Int J Artif Organs* 2012, 35 (3), 191-198. DOI: 10.5301/ijao.5000079.

24. Singelyn, J. M.; DeQuach, J. A.; Seif-Naraghi, S. B.; Littlefield, R. B.; Schup-Magoffin, P. J.; Christman, K. L., Naturally derived myocardial matrix as an injectable scaffold for cardiac tissue engineering. *Biomaterials* 2009, 30 (29), 5409-5416. DOI: 10.1016/j.biomaterials.2009.06.045.

25. Shah, M.; Pawan, K. C.; Copeland, K. M.; Liao, J.; Zhang, G., A Thin Layer of Decellularized Porcine Myocardium for Cell Delivery. *Sci Rep-Uk* 2018, 8. DOI: ARTN 16206 10.1038/s41598-018-33946-2.

26. Gilpin, A.; Yang, Y., Decellularization Strategies for Regenerative Medicine: From Processing Techniques to Applications. *Biomed Research International* 2017. DOI: Artn 9831534 10.1155/2017/9831534.

27. Karsdal, M. A., Biochemistry of Collagens, Laminins and Elastin Structure, Function and Biomarkers Introduction. *Biochemistry of Collagens, Laminins and Elastin: Structure, Function and Biomarkers* 2016, Xix-Xxxiv.

28. Song, W.; Wang, H.; Wu, Q. Y., Atrial natriuretic peptide in cardiovascular biology and disease (NPPA). *Gene* 2015, 569 (1), 1-6. DOI: 10.1016/j.gene.2015.06.029.

29. Brunner-La Rocca, H. P.; Kiowski, W.; Ramsay, D.; Sutsch, G., Therapeutic benefits of increasing natriuretic peptide levels. *Cardiovasc Res* 2001, 51 (3), 510-520.

30. Palmer, B. F.; Clegg, D. J., An Emerging Role of Natriuretic Peptides: Igniting the Fat Furnace to Fuel and Warm the Heart. *Mayo Clinic Proceedings* 2015, 90 (12), 1666-1678. DOI: 10.1016/j.mayocp.2015.08.006.

31. Andenaes, K.; Lunde, I. G.; Mohammadzadeh, N.; Dahl, C. P.; Aronsen, J. M.; Strand, M. E.; Palmero, S.; Sjaastad, I.; Christensen, G.; Engebretsen, K. V. T.; Tonnessen, T., The extracellular matrix proteoglycan fibromodulin is upregulated in clinical and experimental heart failure and affects cardiac remodeling. *Plos One* 2018, 13 (7). DOI: ARTN e0201422 10.1371/journal.pone.0201422.

32. Zheng, Z.; James, A. W.; Li, C. S.; Jiang, W. L.; Wang, J. Z.; Chang, G. X.; Lee, K. S.; Chen, F.; Berthiaume, E. A.; Chen, Y.; Pan, H. C.; Chen, E. C.; Li, W. M.; Zhao, Z. H.; Zhang, X. L.; Ting, K.; Soo, C., Fibromodulin reduces scar formation in adult cutaneous wounds by eliciting a fetal-like phenotype. *Signal Transduct Tar* 2017, 2. DOI: UNSP e17050 10.1038/sigtrans.2017.50.

33. Zheng, Z.; Jian, J.; Velasco, 0.; Hsu, C. Y.; Zhang, K.; Levin, A.; Murphy, M.; Zhang, X.; Ting, K.; Soo, C., Fibromodulin Enhances Angiogenesis during Cutaneous Wound Healing. *Prs-Glob Open* 2014, 2 (12). DOI: ARTN e275 10.1097/GOX.0000000000000243.

34. Huleihel, L.; Bartolacci, J. G.; Dziki, J. L.; Vorobyov, T.; Arnold, B.; Scarritt, M. E.; Molina, C. P.; LoPresti, S. T.; Brown, B. N.; Naranjo, J. D.; Badylak, S. F., Matrix-Bound Nanovesicles Recapitulate Extracellular Matrix Effects on Macrophage Phenotype. *Tissue Eng Pt A* 2017, 23 (21-22), 1283-1294. DOI: 10.1089/ten.tea.2017.0102.

35. Hussey, G. S.; Dziki, J. L.; Lee, Y. C.; Bartolacci, J. G.; Behun, M.; Turnquist, H. R.; Badylak, S. F., Matrix bound nanovesicle-associated IL-33 activates a pro-remodeling macrophage phenotype via a non-canonical, ST2-independent pathway. *Journal of Immunology and Regenerative Medicine* 2019, 3, 26-35. DOI: 10.1016/j.regen.2019.01.001.

36. Mora-Navarro, C.; Badileanu, A.; Gracioso Martins, A. M.; Ozpinar, E. W.; Gaffney, L.; Huntress, I.; Harrell, E.; Enders, J. R.; Peng, X.; Branski, R. C.; Freytes, D. O., Porcine Vocal Fold Lamina Propria-Derived Biomaterials Modulate TGF-β1-Mediated Fibroblast Activation in Vitro. Acs Biomater Sci Eng 2020. DOI: 10.1021/acsbiomaterials.9b01837.

37. Tse, J. R.; Long, J. L., Microstructure Characterization of a Decellularized Vocal Fold Scaffold for Laryngeal Tissue Engineering. *Laryngoscope* 2014, 124 (8), E326-E331. DOI: 10.1002/lary.24605.

38. Sarker, B.; Singh, R.; Silva, R.; Roether, J. A.; Kaschta, J.; Detsch, R.; Schubert, D. W.; Cicha, I.; Boccaccini, A. R., Evaluation of Fibroblasts Adhesion and Proliferation on Alginate-Gelatin Crosslinked Hydrogel. *Plos One* 2014, 9 (9). DOI: ARTN e107952 10.1371/journal.pone.0107952.

39. Christensen, G.; Herum, K. M.; Lunde, I. G., Sweet, yet underappreciated: Proteoglycans and extracellular matrix remodeling in heart disease. *Matrix Biol* 2019, 75-76, 286-299. DOI: 10.1016/j.matbio.2018.01.001.
40. U.S. Pat. No. 9,084,722 B2 issued Jul. 21, 2015 to Gilbert et al.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. An automated tissue decellularization system, the system comprising:
a bioreactor;
a filtration device, optionally a lateral inline filtration device;
a stirring mechanism;
a temperature-controlled system for temperature adjustment and control of the bioreactor, and
a fluid control system comprising a dosing system and/or one or more dosing pumps configured to automatically supply one or more reagents to the bioreactor, and/or to apply a feedback for in situ solubilization of ECM for downstream scaffold production, and/or remove waste from the bioreactor,
wherein the automated decellularization bioreactor system is configured to decellularize a tissue, optionally a soft tissue, to produce an extracellular matrix (ECM) scaffold and/or to produce solubilized downstream ECM-products.

2. The automated decellularization bioreactor system of claim 1, wherein the bioreactor comprises a series of bioreactors or a plurality of bioreactors.

3. The automated decellularization bioreactor system of claim 1, wherein the filtration device comprises a lateral inline filtration device or a fritted filter.

4. The automated decellularization bioreactor system of claim 1, further comprising an in-line monitoring system, optionally wherein the in-line monitoring system comprises a spectroscopy-based monitoring system, further optionally wherein the spectroscopy-based monitoring system comprises fluorescence, luminescence, absorbance and/or Raman.

5. The automated decellularization bioreactor system of claim 4, wherein the spectroscopy-based monitoring system is configured to measure nucleic acid removal in the decellularization system, optionally wherein the monitoring is in real-time, optionally wherein the monitoring comprises measurement of an absorbance at 260 nm.

6. The automated decellularization bioreactor system of claim 1, further comprising a remote dosing controller configured to control the automated tissue decellularization system.

7. Automated decellularization bioreactor system of claim 1, further comprising a filter component configured to maintain a decellularized tissue within the filtration device while simultaneously allowing the removal of a liquid filtrated phase, optionally solubilized ECM-products or waste.

8. The automated decellularization bioreactor system of claim 1, further comprising a plurality of ports, where the plurality of ports are configured for sampling, effluent removal and/or waste removal, optionally wherein the plurality of ports are configured as a sample port for continuous sampling/monitoring process.

9. The automated decellularization bioreactor system of claim 1, further comprising a waste removal port positioned on the filtration device.

10. The automated decellularization bioreactor system of claim 1, further comprising a pump configured to remove waste from the filtration device via the waste removal port and/or a pump configured to manage a feedback system configured for downstream ECM-solubilization and/or to produce solubilized downstream ECM-products.

11. The automated decellularization bioreactor system of claim 1, wherein the stirring mechanism comprises one or more magnetic stir bars and a magnetic stir plate and/or wherein the stirring mechanism comprises a rotating filtration system pre-loaded with weights and/or beads, such as sterile weights-beads, optionally, wherein the stirring mechanism further comprises one or more impellers and/or baffles configured to increase turbulence for improved stirring and mixing.

12. The automated decellularization bioreactor system of claim 1, wherein the dosing system comprises one or more pumps connected in parallel or in series by one or more tubes, wherein the one or more tubes converge on a single input into the inline filtration device, optionally wherein the one or more pumps comprise one or more peristaltic pumps.

13. The automated decellularization bioreactor system of claim 1, wherein the one or more dosing pumps are connected to individual reagent reservoirs.

14. The automated decellularization bioreactor system of claim 1, wherein the reagents are selected from the group comprising enzymatic solutions, detergents, alcohols for delipidation, acids or bases, and/or combinations thereof.

15. The automated decellularization bioreactor system of claim 1, further comprising a manifold configured to arrange the one or more tubes from the one or more dosing pumps to prevent unwanted interactions between reagents.

16. The automated decellularization bioreactor system of claim 1, wherein the system is configured to provide adjustability of an exposure time, type of reagent, and/or order in which the tissue is exposed to a reagent.

17. A method of producing extracellular matrix (ECM) based biomaterials or ECM scaffolds, the method comprising:
providing an automated decellularization bioreactor system of claim 1;
performing a size-reducing pre-treating step of a tissue, optionally a soft tissue, to increase surface area of the tissue; and
processing the pre-treated tissue through the automated decellularization bioreactor system.

18. The method of claim 17, wherein the size-reducing pre-treating step comprises grinding, mincing, chopping and/or micronization of the tissue.

19. The method of claim 17, wherein the soft tissue comprises heart tissue, vocal fold lamina propria, lung tissue, skeletal muscle tissue, pancreatic tissue, oral mucosa, supraglottic and dermis tissue, optionally wherein the tissue is provided from different source donors, further optionally wherein the source donors are human, murine, porcine or bovine source donors.

20. The method of claim 17, further comprising a series of hypotonic and/or hypertonic short washes and mechanical dissociation of the tissue via stirring.

21. The method of claim 17, wherein processing the tissue through the automated decellularization bioreactor system comprises exposing the tissue to a series of reagents selected from the group comprising enzymatic solutions, detergents, alcohols for delipidation, acid or base formulations, and/or combinations thereof.

22. The method of claim 17, wherein the ECM scaffolds are produced in a reduced time compared to other ECM production methods, and wherein the produced ECM scaffolds maintain cytocompatibility, optionally wherein the produced ECM scaffolds have an overall higher abundance of ECM-related proteins compared to other ECM production methods.

23. The method of claim 17, wherein the ECM scaffolds are produced in three hours or less.

24. The method of claim 17, comprising scaling up the method and/or pursuing larger ECM-production from soft tissues.

25. An extracellular matrix (ECM) based biomaterial or ECM scaffold produced by claim 17.

26. The ECM based biomaterial or ECM scaffold of claim 25, wherein the ECM scaffold comprises a reduced nuclei content compared to a native tissue, optionally a native soft tissue.

27. The ECM based biomaterial or ECM scaffold of claim 25, wherein the ECM scaffold comprises a reduced double-stranded DNA (dsDNA) content as compared to a native tissue, optionally a native soft tissue, optionally wherein the ECM scaffold comprises less than about 2 ug dsDNA per mg of dry weight ECM as measured with the protocol Double stranded DNA (dsDNA) Quantification disclosed herein.

28. The ECM based biomaterial or ECM scaffold of claim 25, wherein the ECM scaffold comprises a higher fibrillar collagens (Types I, II, III, V & XI) content per milligram of dry decellularized ECM compared to classical manual meth-ods, optionally wherein the ECM scaffold comprises larger than about 475 ug of fibrillar collagens (Types I, II, III, V & XI) per mg of dry weight decellularized ECM.

29. The ECM based biomaterial or ECM scaffold of claim 25, wherein the ECM scaffold comprises proteoglycans, glycoproteins at different abundance as compared to a native tissue, optionally a native soft tissue; or wherein the ECM scaffold comprises increased proteoglycan and glycoproteins as compared to the same tissue decellularized with longer protocols, optionally other ECM derivation methods.

30. The ECM based biomaterial or ECM scaffold of claim 25, wherein the ECM scaffold comprises increased keratin, collagens, fibrin, and/or other ECM-related proteins as compared to other decellularized ECM from the same tissue type and/or source.

31. The ECM based biomaterial or ECM scaffold of claim 25, wherein the ECM scaffold comprises an injectable biomaterial of a particle size according to a filter mesh used within the bioreactor, optionally wherein the particle size is less than about 30 um, less than about 100 um, or less than about 300um.

32. The ECM based biomaterial or ECM scaffold of claim 25, wherein the ECM scaffold comprises a biomaterial adapted for aerosolization.

33. A decellularized scaffold end product, optionally comprising a heart tissue, a vocal fold lamina propria (VFLP) or supraglottic (SG), comprising an ECM scaffold of claim 25, and having an overall higher abundance of ECM-related proteins compared to other ECM production methods.

* * * * *